(12) United States Patent
Kumar

(10) Patent No.: US 6,382,977 B1
(45) Date of Patent: May 7, 2002

(54) SNAP-IN IMPRESSION COPING

(75) Inventor: Ajay Kumar, Palmdale, CA (US)

(73) Assignee: Nobel Biocare USA, Inc., Yorba Linda, CA (US)

( * ) Notice: Subject to any disclaimer, the term of this patent is extended or adjusted under 35 U.S.C. 154(b) by 0 days.

(21) Appl. No.: 09/605,619

(22) Filed: Jun. 28, 2000

Related U.S. Application Data

(60) Provisional application No. 60/186,535, filed on May 2, 2000.

(51) Int. Cl.[7] .................................................. A61C 9/00
(52) U.S. Cl. ....................................... 433/214; 433/173
(58) Field of Search ................................. 433/172, 173, 433/174, 177, 213, 214

(56) References Cited

U.S. PATENT DOCUMENTS

| | | | |
|---|---|---|---|
| 3,760,502 A | 9/1973 | Hirsch | |
| 4,158,256 A | 6/1979 | Wiland | |
| 4,324,549 A | 4/1982 | Madray | 433/169 |
| 4,380,436 A | 4/1983 | Kipp | 433/182 |
| 4,416,629 A | 11/1983 | Mozsary et al. | 433/174 |
| 4,540,367 A | 9/1985 | Sulc | 433/181 |
| 4,571,185 A | 2/1986 | Rota | 433/173 |
| 4,681,542 A | 7/1987 | Baum | 433/172 |
| 4,715,817 A | 12/1987 | Zuest et al. | 433/181 |
| 4,722,688 A | 2/1988 | Lonca | 433/173 |
| 5,030,094 A | 7/1991 | Nardi et al. | 433/169 |
| 5,030,096 A | 7/1991 | Hurson et al. | 433/173 |
| 5,125,840 A | 6/1992 | Durr et al. | 433/173 |
| 5,211,561 A | 5/1993 | Graub | 433/169 |
| 5,246,368 A | 9/1993 | Sillard | 433/167 |
| 5,417,570 A | 5/1995 | Zuest et al. | 433/177 |
| 5,437,551 A | 8/1995 | Chalifoux | 433/173 |
| 5,492,471 A | 2/1996 | Singer | 433/172 |
| 5,556,280 A | 9/1996 | Pelak | 433/172 |
| 5,630,717 A | 5/1997 | Zuest et al. | 433/172 |
| 5,688,123 A | 11/1997 | Meiers et al. | 433/173 |
| 5,704,788 A | 1/1998 | Milne | 433/173 |
| 5,733,123 A | 3/1998 | Blacklock et al. | 433/173 |
| 5,759,036 A | * 6/1998 | Hinds | 433/173 |
| 5,762,500 A | 6/1998 | Lazarof | 433/213 |
| 5,782,918 A | 7/1998 | Klardie et al. | 433/172 |
| 5,829,981 A | 11/1998 | Ziegler | 433/214 |
| 5,888,218 A | * 3/1999 | Folsom | 433/172 |
| 5,897,320 A | 4/1999 | Gittleman | 433/180 |
| 5,904,483 A | 5/1999 | Wade | 433/173 |
| 5,947,736 A | 9/1999 | Behrend | 433/214 |
| 6,012,923 A | 1/2000 | Bassett et al. | 433/172 |
| 6,030,219 A | 2/2000 | Zuest et al. | 433/181 |
| 6,068,478 A | 5/2000 | Grande et al. | 433/172 |

FOREIGN PATENT DOCUMENTS

| | | |
|---|---|---|
| WO | WO 96/29019 | 9/1996 |
| WO | WO 98/52490 | 11/1998 |
| WO | WO 00/02497 | 1/2000 |

* cited by examiner

*Primary Examiner*—Cary E. O'Connor
(74) *Attorney, Agent, or Firm*—Knobbe, Martens Olson & Bear, LLP

(57) ABSTRACT

An impression coping is provided for taking an impression of an implant installed in a patient's mouth. The impression coping comprises a proximal end and a distal end. The proximal end is adapted to be inserted within a coronal opening formed in the implant and has an anti-rotation formation cooperating with a corresponding anti-rotation formation formed in the implant for preventing relative rotation of the coping and implant. The coping further includes resilient fingers for engaging corresponding surfaces formed within the coronal opening of the implant. The distal end of the coping includes an impression portion adapted to be embedded in a dental impression material for taking a dental impression thereof.

69 Claims, 20 Drawing Sheets

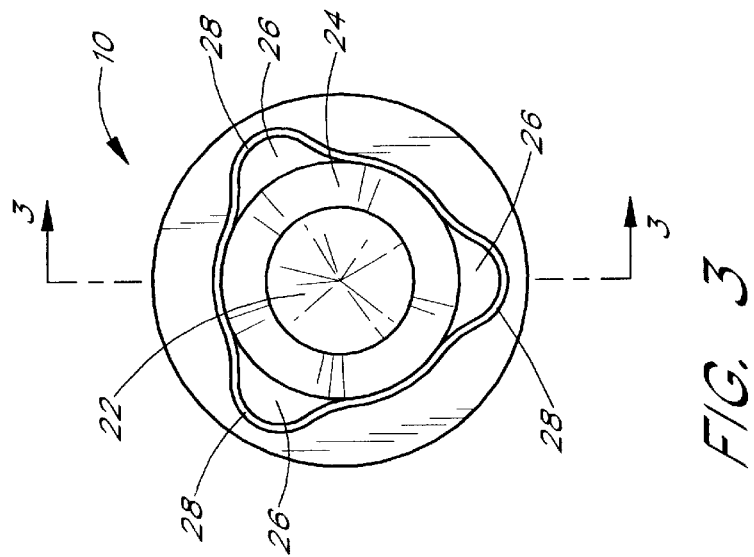
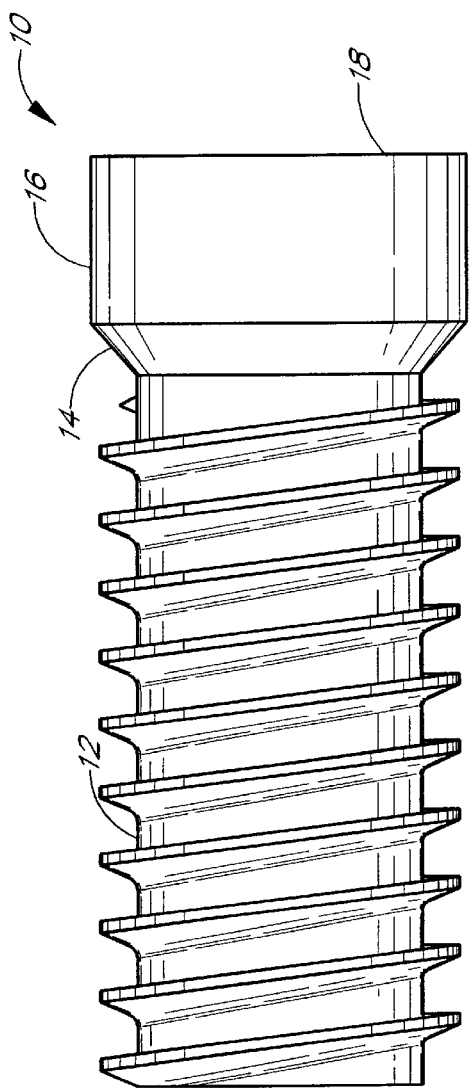
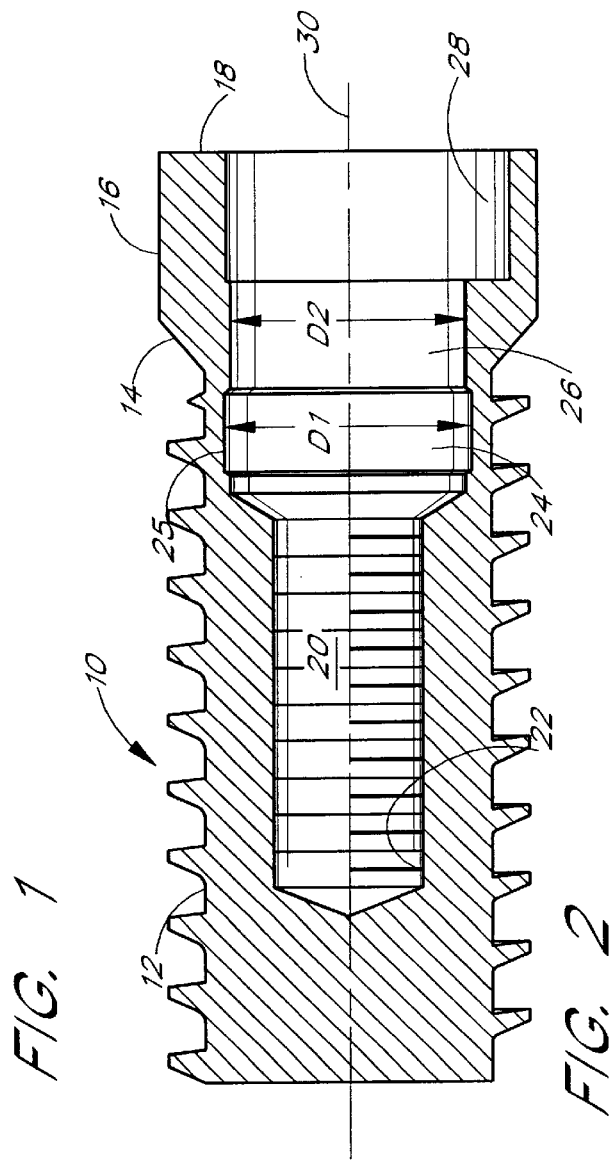

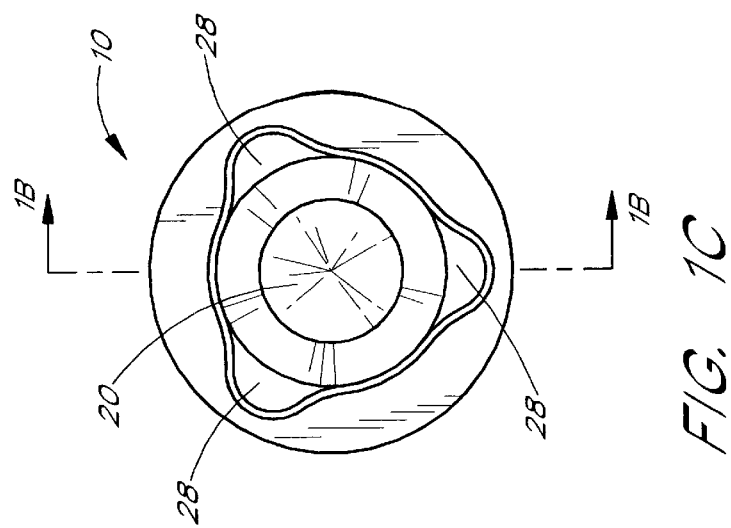
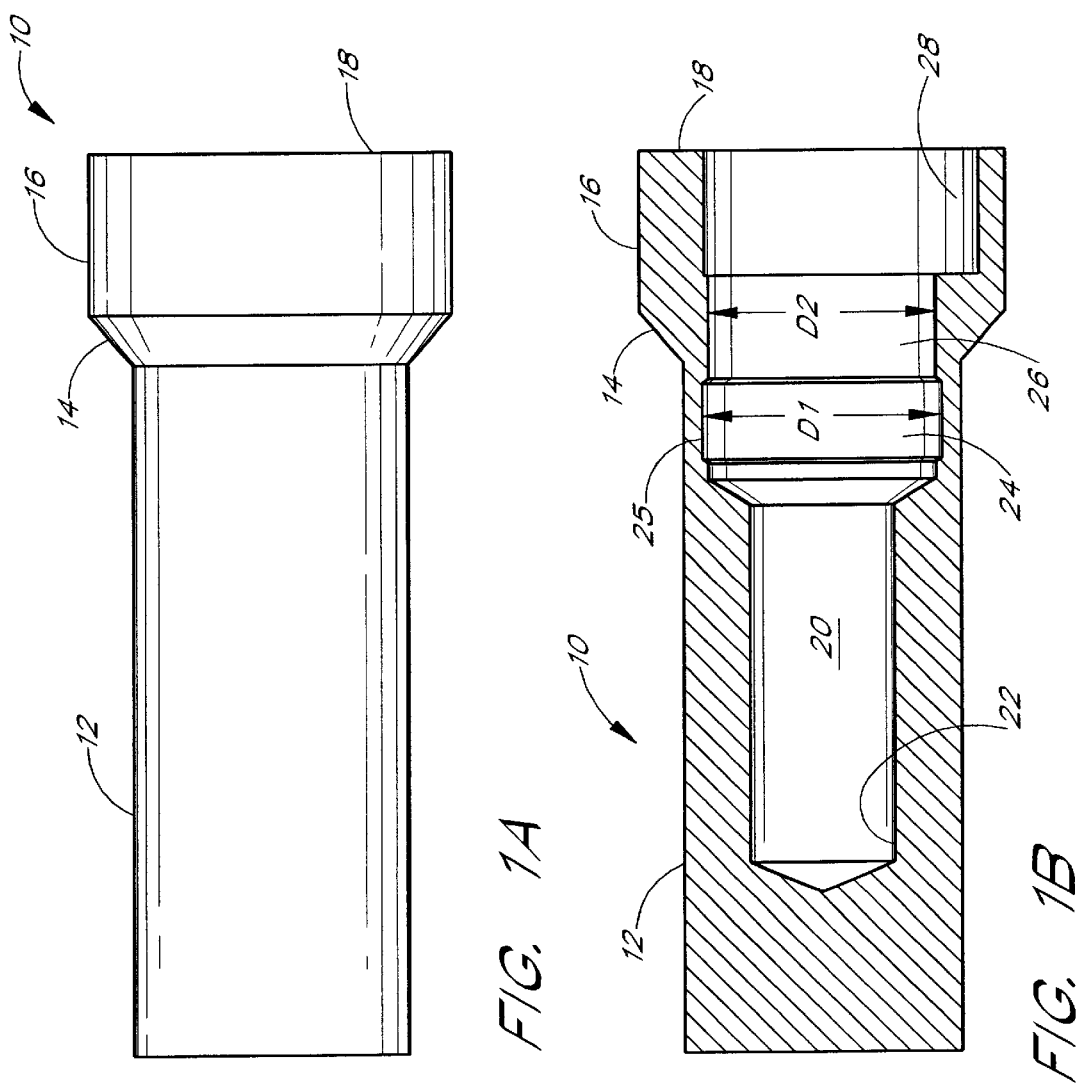

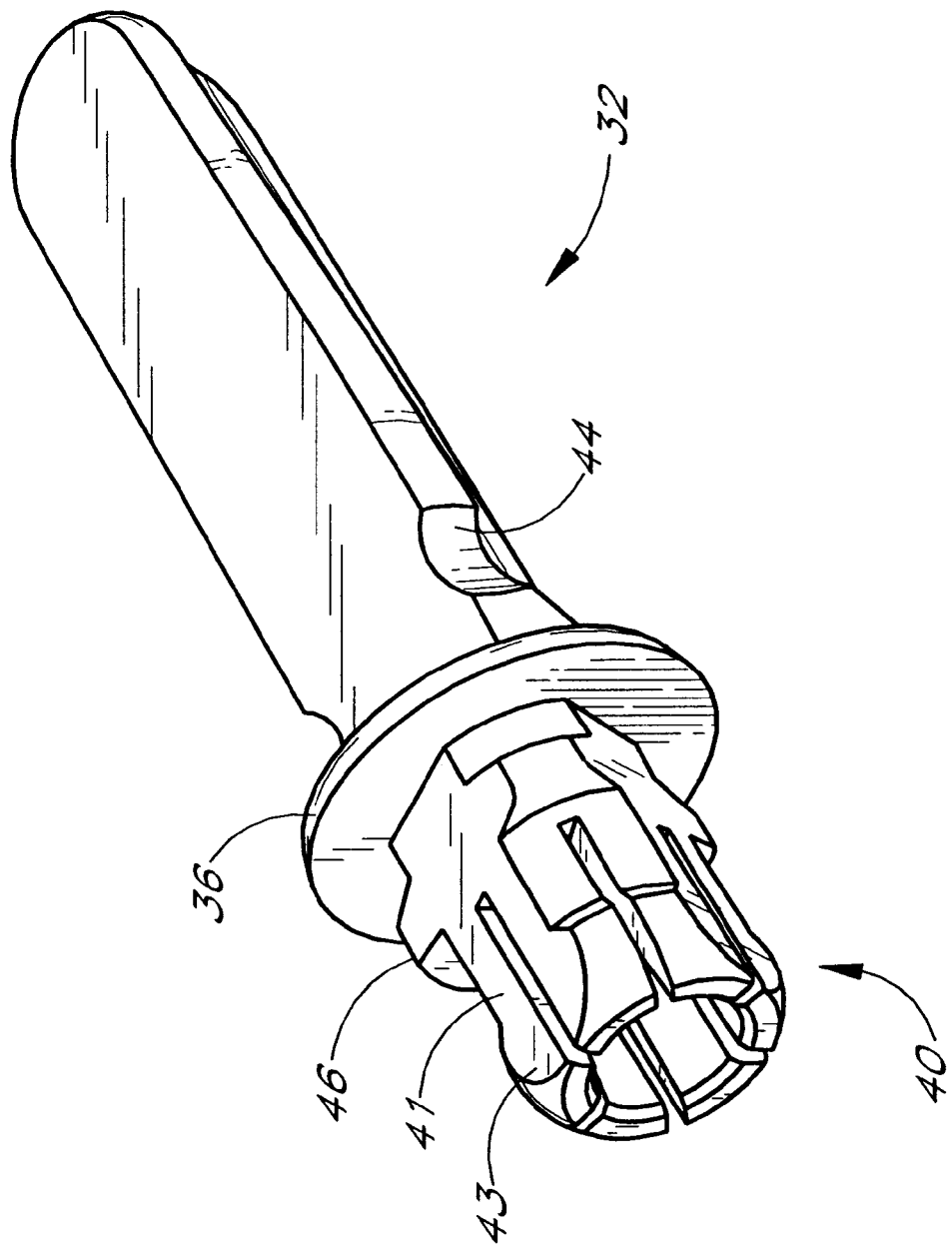

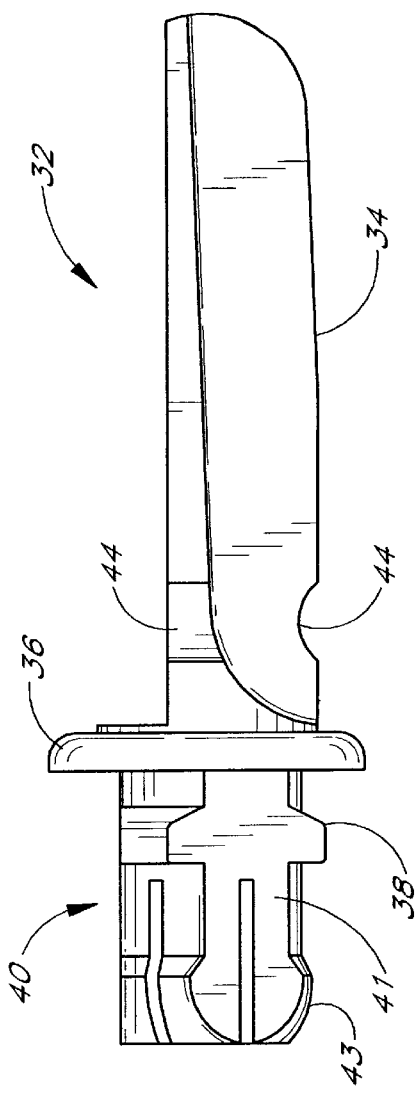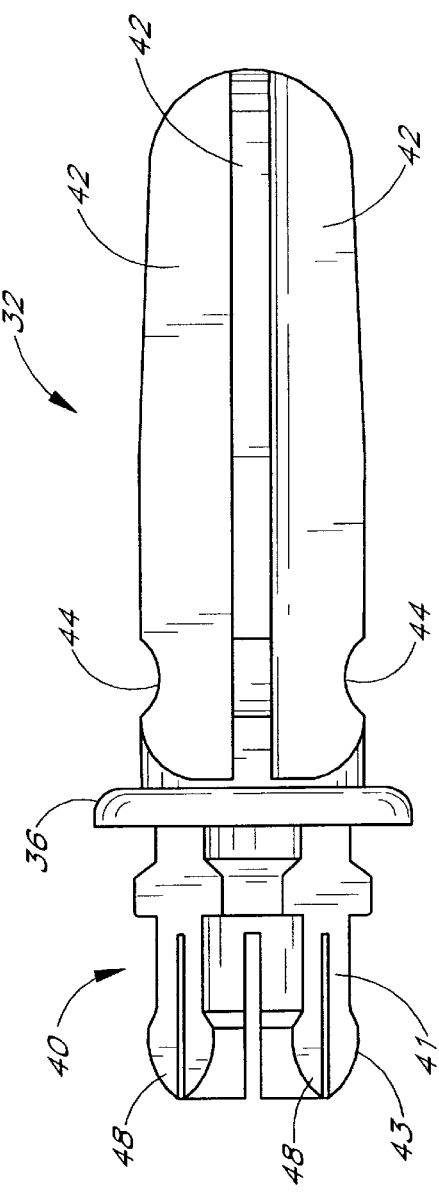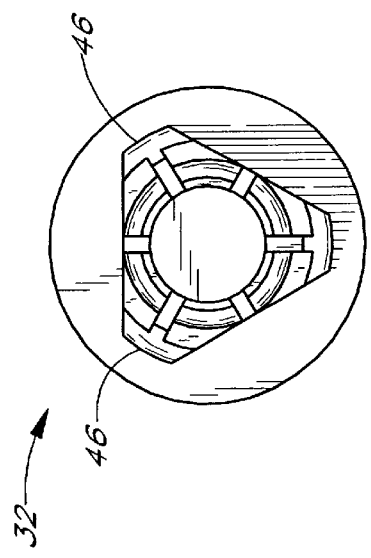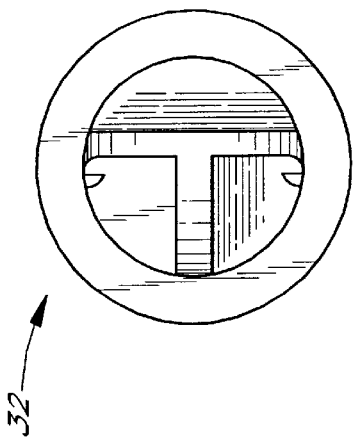

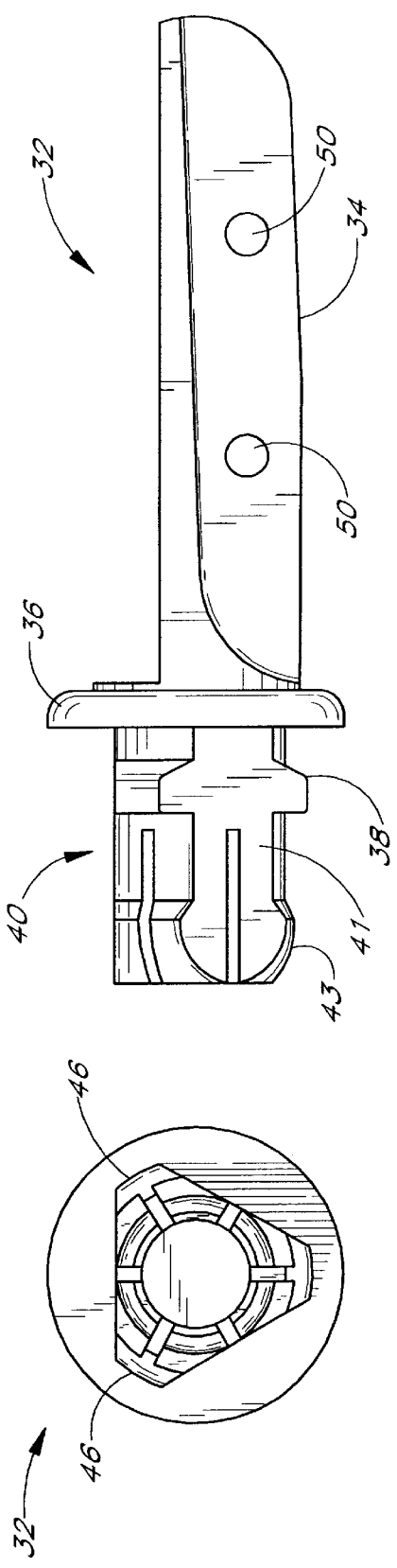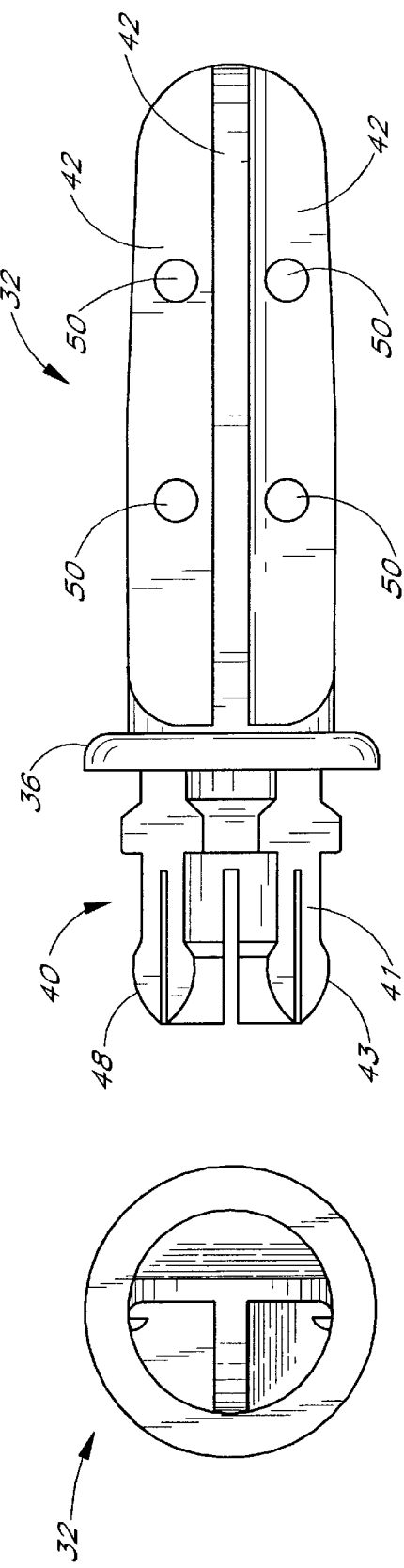

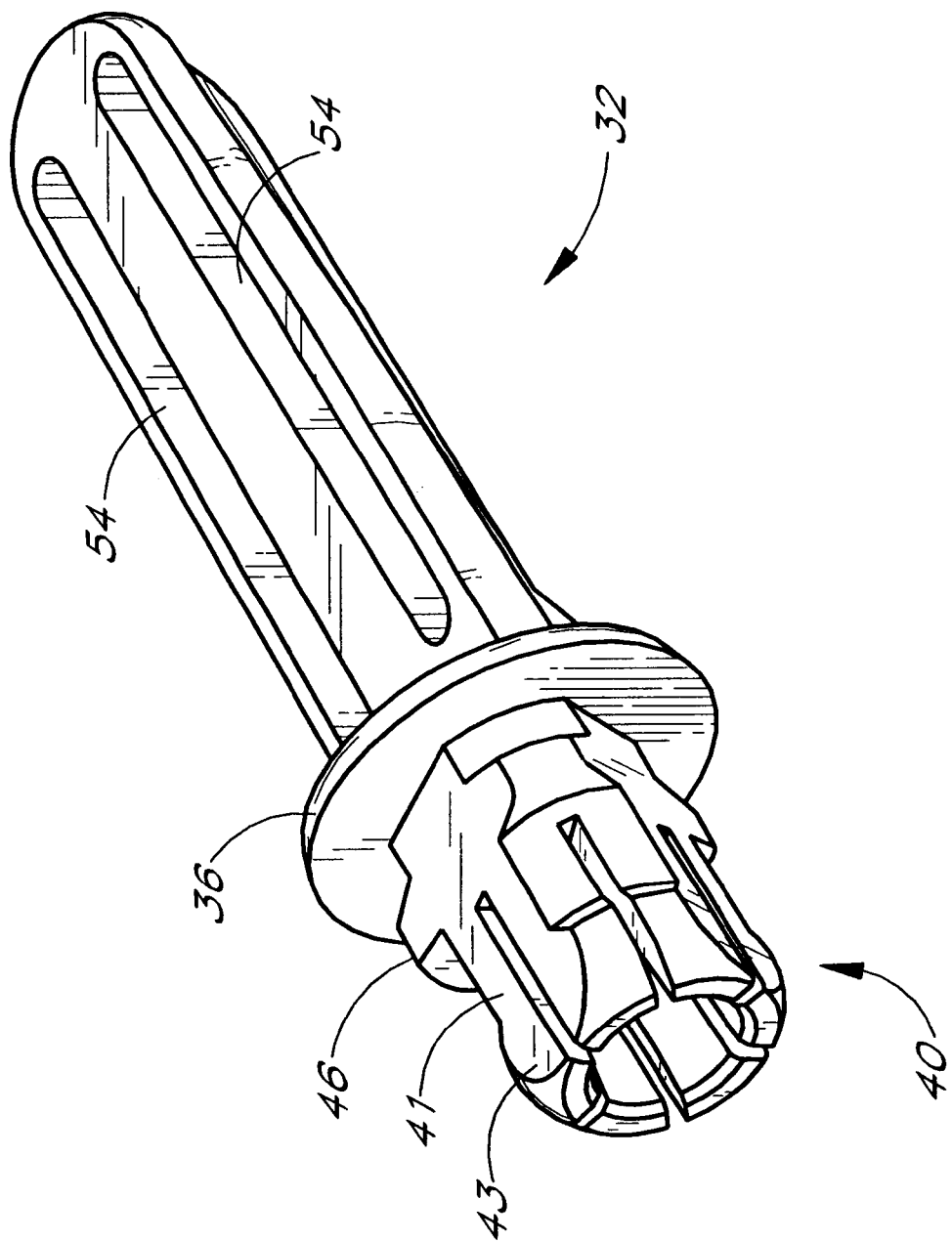

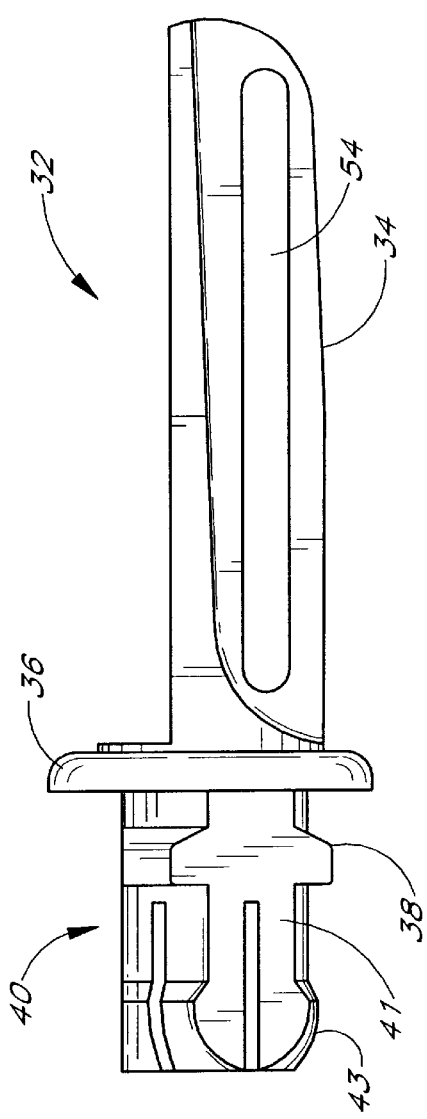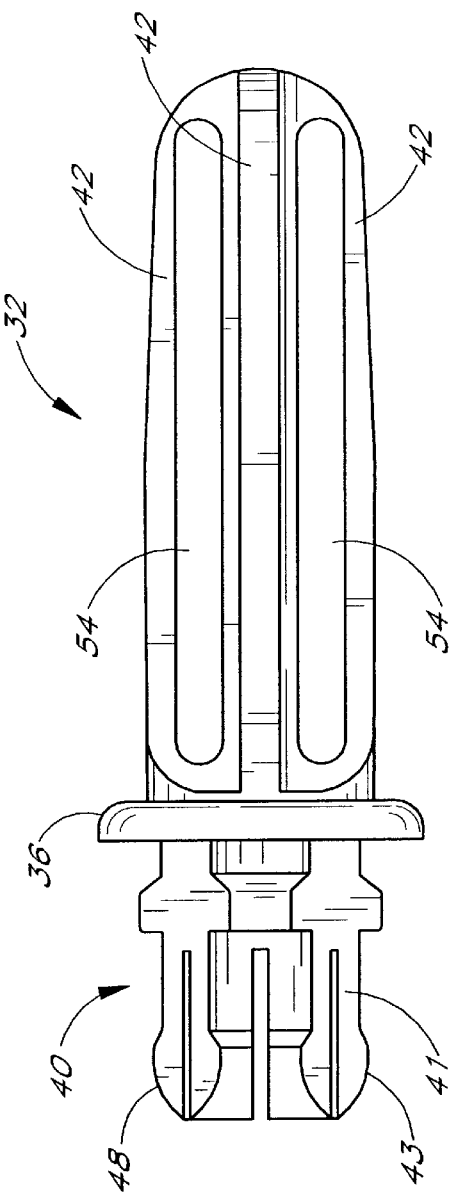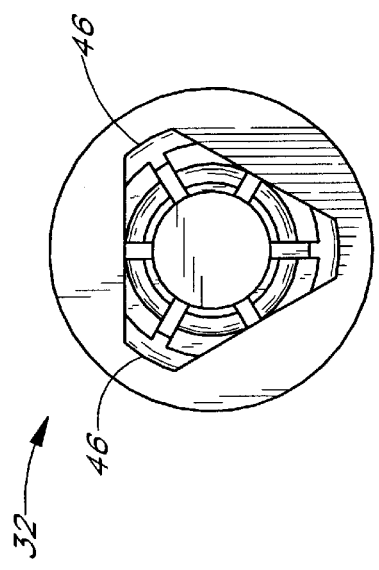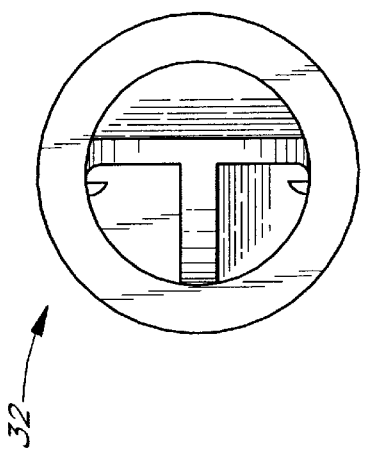
FIG. 14C
FIG. 14B
FIG. 14D
FIG. 14E

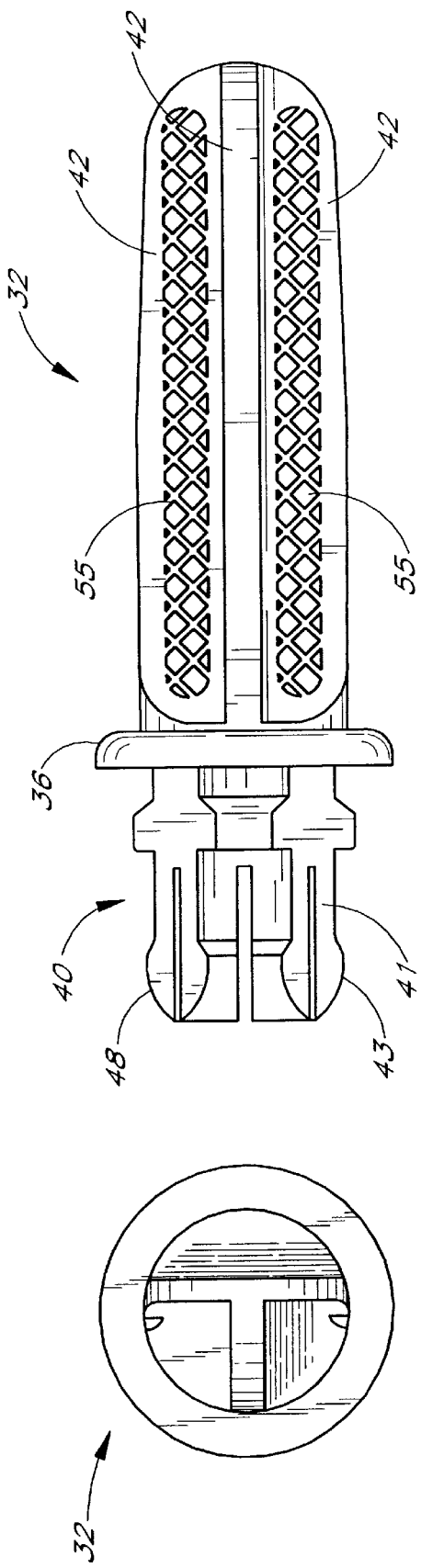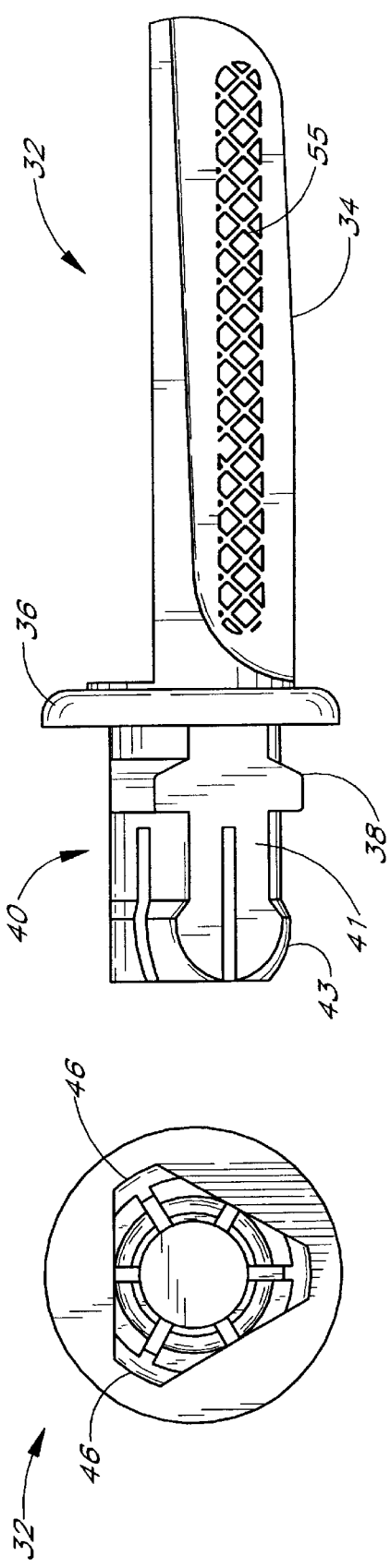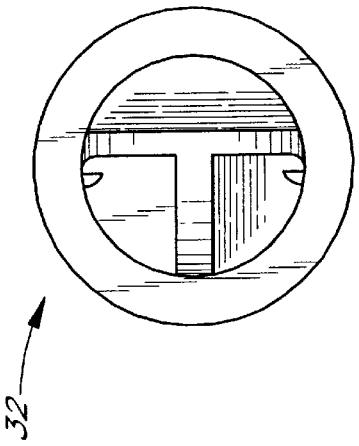

SNAP-IN IMPRESSION COPING

CROSS REFERENCE TO RELATED APPLICATIONS

The present application claims priority and benefit under 35 U.S.C. §119(e) of U.S. Provisional Patent Application Ser. No. 60/186,535, filed March 2, 2000.

BACKGROUND OF THE INVENTION

1. Field of the Invention

This invention relates to dental impression copings of the type used in implant dentistry to take impressions of a dental implant site from which accurate models can be constructed. More particularly, the invention relates to an improved pick-up type impression coping, which utilizes a snap fit attachment coping with anti-rotational properties.

2. Description of the Related Art

Implant dentistry involves the restoration of edentulous area(s) in a patient's mouth using artificial components, including typically an implant fixture or root and a prosthetic tooth and/or final abutment which is secured to the implant fixture. According to state of the art techniques, the process for restoring a tooth and its root is carried out generally in three stages.

Stage I involves implanting the dental implant fixture into the bone of a patient's jaw. The oral surgeon first accesses the patient's jawbone through the patient's gum tissue and removes any remains of the tooth to be replaced. Next, the specific site in the patient's jaw where the implant will be anchored is widened by drilling and/or reaming to accommodate the width of the dental implant fixture to be implanted. Then, the dental implant fixture is inserted into the hole in the jawbone, typically by screwing, although other techniques are known for introducing the implant in the jawbone.

The implant fixture itself is typically fabricated from pure titanium or a titanium alloy. Such materials are known to produce osseointegration of the fixture with the patient's jawbone. The dental implant fixture also typically includes a hollow threaded bore through at least a portion of its body and extending out through its proximal end which is exposed through the crestal bone for receiving and supporting the final tooth prosthesis and/or various intermediate components or attachments.

After the implant is initially installed in the jawbone a temporary healing cap is secured over the exposed proximal end in order to seal the internal bore. The patient's gums are then sutured over the implant to allow the implant site to heal and to allow desired osseointegration to occur. Complete osseointegration typically takes anywhere from four to ten months.

During stage II, the surgeon re-accesses the implant fixture by making an incision through the patient's gum tissues. The healing cap is then removed, exposing the proximal end of the implant. A mold or impression is then taken of the patient's mouth to accurately record the position and orientation of the implant within the mouth. This is used to create a plaster model or analogue of the mouth and/or the implant site and provides the information needed to fabricate the prosthetic replacement tooth and any required intermediate prosthetic components. Stage II is typically completed by attaching to the implant a temporary healing abutment or other transmucosal component to control the healing and growth of the patient's gum tissue around the implant site.

Stage III involves fabrication and placement of a cosmetic tooth prosthesis to the implant fixture. The plaster analogue provides laboratory technicians with a model of the patient's mouth, including the orientation of the implant fixture relative to the surrounding teeth. Based on this model, the technician constructs a final restoration. The final step in the restorative process is replacing the temporary healing abutment with the final restoration.

To achieve optimal results in terms of overall aesthetics and bio-functioning ability of the tooth restoration, it is essential in stage II that the plaster analogue accurately reflect the true position and orientation of the implant in the patient's mouth and that in stage III such position and orientation is faithfully replicated when securing the final tooth restoration to the implant. To help achieve this accuracy and faithful replication, one or more indexing means are typically provided on the proximal end of the implant and corresponding mating indexing means are formed on the various mating components which are adapted to be fitted to the implant. Such indexing means provide desired orientation of the implant and mating components relative to one another and also prevent undesired rotation.

Such indexing means frequently take the form of a hexagonal boss or recess ("hex") formed on the proximal portion of the implant exposed through the crestal bone. For externally threaded implants the hex may also be used to engage a driving tool for driving the implant into an internally threaded bore or osteotomy prepared in the patient's jawbone (mandible or maxilla). When the implant is fully installed in a patient's jawbone the hex or other indexing means is typically exposed through the crestal bone so that accurate indexing may be provided between the implant and the final prosthesis and/or various intermediate mating prosthetic components.

As noted above, during stage II of the dental restorative process a mold or impression is taken of the patient's mouth to accurately record the position(s) and orientation(s) of the indexing means within the mouth at the implant site(s) and to thereby providing the information needed to fabricate the restorative replacement(s) and/or intermediate prosthetic components. According to the state of the art, this is done using a casting or impression material formed of a soft resin—typically polyvinylsiloxane or polyether—which can be applied over the implant site using a suitable impression tray and allowed to cure in situ. The impression material is sufficiently resilient such that it can be removed from the patient's mouth after it is cured (or partially cured) while at the same time retaining an accurate impression of the patient's mouth and particularly the implant site.

However, because the indexing means of the implant is typically quite small and may be recessed partially beneath the gums of a patient, a secondary or intermediate impression element is typically used to help transfer accurately the orientation of the indexing means of the implant. This intermediate impression element is commonly called a "coping" or "impression coping." Examples of impression copings as found in the prior art are shown in U.S. Pat. No. 4,955,811 to Lazzara et al., e.g., FIGS. 5, 6, and 9. There are primarily two types of such impression copings used today—so-called "transfer" impression copings and so-called "pick-up" impression copings. Both are conveniently adapted to be screw-retained to the implant. The choice of which technique is to use (open tray vs. closed tray) is based primarily on individual patient characteristics and the clinician's preference.

Conventional transfer impression copings have an impression portion adapted to form a unique or indexed impression in the impression material and a base portion having mating indexing means adapted to mate with the exposed indexing means of the implant. In use, the impression coping is temporarily secured to the exposed proximal end of the implant fixture such that the mating indexing means of the impression coping and implant are interlockingly mated to one another. Typically, a threaded screw or bolt is used to temporarily secure the impression coping to the implant fixture.

Once the impression coping(s) is secured to the implant fixture(s), an impression of the coping(s) relative to the surrounding teeth is taken. A U-shaped impression tray filled with an impression material is placed in the patient's mouth over the implant site. The patient bites down on the tray, squeezing the impression material into the implant site and around the impression coping(s). Within a few minutes, the impression material cures or hardens to a flexible, resilient consistency. The impression tray is then removed from the patient's mouth to reveal an impression of the implant site and the impression coping(s). The restorative dentist then removes the impression coping(s) by unthreading the screw from the implant. The coping(s) is then removed from the patient's mouth and is transferred back into the impression material, being careful to preserve the proper orientation of the indexing means. This impression method using transfer impression copings is commonly referred to as the "closed-tray" technique. While the closed-tray technique is simple in its design and execution, it is sometimes prone to inaccuracies where sufficient care is not taken during the step of reinserting the impression coping(s) into the impression material.

Conventional pick-up impression copings are similar to transfer copings described above, except that pick-up impression copings typically include an embedment portion adapted to non-removably embed the impression coping securely within the impression material. Typically, the embedded portion comprises a protuberant "lip" or similar embedment projection at their coronal aspect, such that the diameter of the lip is larger than the diameter of the immediately adjacent (more apical) area of the transfer coping. This allows for "grabbing" or retention of the impression material as it is being removed from the patient's mouth. In this case, once the impression is taken the tray is removed from the patient's mouth, the impression coping(s) remain in the impression material and are "picked up" and pulled away from the patient's mouth along with the impression material. To facilitate such pick-up removal of conventional screw-secured impression copings, the tray is provided with one or more apertures or openings through which a tool may be inserted to loosen the screw or bolt securing each coping. Thus, this impression technique is commonly referred to as the "open-tray" technique. The open-tray technique is particularly well suited for multi-site dental restoration procedures, especially when there is a large divergence angle between multiple adjacent implants, or when the dentist wishes to utilize a verification stent to check the accuracy of the working stone model. The open-tray technique is generally preferred for accuracy, but do to the need to cut holes or apertures in the tray, it is more complex. As a result, it often takes more time to prepare and execute.

SUMMARY OF THE INVENTION

In one embodiment the present invention provides an impression coping for taking an accurate dental impression of an implant installed in a patient's jawbone. The impression coping has a proximal end and a distal end. The proximal end is configured and adapted to be secured to the implant and includes a protrusion that is sized and dimensioned to engage a recess formed in the implant. The coping also includes an indexing boss and/or recess formed for interlockingly engaging a corresponding mating indexing boss and/or recess formed on the implant. The distal end includes at least one annular recess, slot(s), wings, button, ball, or a criss-cross configuration for retaining the impression coping in the impression material. The coping may be configured and used as either a transfer coping or pick-up coping, as desired.

In another embodiment the present invention provides an impression coping for taking an impression of an implant installed in a patient's mouth. The impression coping comprises a proximal end and a distal end. The proximal end is adapted to be inserted within a coronal opening formed in the implant and has anti-rotation means cooperating with corresponding anti-rotation means formed in the implant for preventing relative rotation of the coping and implant. The coping further includes resilient fingers for engaging corresponding surfaces formed within the coronal opening of the implant. The distal end of the coping includes an impression portion adapted to be embedded in a dental impression material for taking a dental impression thereof. The coping may be configured and used as either a transfer coping or pick-up coping.

In yet another embodiment the present invention provides an impression coping for recording the position and orientation of an implant installed in a patient's jawbone. The impression coping comprises a proximal end and a distal end. The proximal end is configured with one or more resilient prongs adapted to be inserted into a coronal opening formed in the implant and to snappingly engage and secure the coping to the implant. The proximal end also includes an indexing boss or recess formed therein for interlockingly engaging a corresponding mating indexing boss or recess formed on the implant. The distal end includes an impression portion for embedding in an impression material for taking a dental impression. The coping may be configured and used as either a transfer coping or pick-up coping, as desired.

In yet another embodiment the present invention provides an impression coping for recording the position and orientation of a dental implant installed in a patient's mouth. The impression coping includes a first end adapted to be snappingly and anti-rotationally mated to the implant and a second end including one or more blade portions adapted to be embedded in an impression material for taking a dental impression. The coping may be configured and used as either a transfer coping or pick-up coping, as desired.

In yet another embodiment the present invention provides an impression coping for recording the position and orientation of a dental implant installed in a patient's mouth. The impression coping is snappingly and anti-rotationally mated to the implant and comprises at least one blade portion for embedment in an impression material for taking a dental impression thereof. The coping may be configured and used as either a transfer coping or pick-up coping, as desired.

In yet another embodiment the present invention provides an impression coping for recording the position and orientation of an implant installed in a patient's jawbone. The impression coping comprises a proximal end and a distal end. The proximal end is sized and adapted to matingly and anti-rotationally engage the implant. The proximal end also has resilient fingers for snappingly mating with corresponding recesses formed within a coronal opening in the implant. The distal end comprises a generally elongated impression portion including one or more substantially flat blade portions extending radially therefrom. The coping may be configured and used as either a transfer coping or pick-up coping, as desired.

In yet another embodiment the present invention provides an impression coping for taking an impression of an implant installed in a patient's mouth. The impression coping comprises a proximal end and a distal end. The proximal end is sized and adapted to be inserted within a coronal opening formed in the implant. The proximal end further includes anti-rotation means cooperating with corresponding anti-rotation means formed on the implant for preventing relative rotation of the coping and implant when the coping is inserted in the implant. The coping further includes resilient snap means for snappingly engaging corresponding surfaces formed within the coronal opening of the implant. The distal end of the coping includes an impression portion adapted to be embedded in a dental impression material for taking a dental impression thereof. The coping may be configured and used as either a transfer coping or pick-up coping, as desired.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

These and other features of the invention will now be described with reference to the drawings of the preferred embodiments, which are intended to illustrate and not to limit the invention, and in which:

FIG. 1 is a side view of a dental implant having certain features and advantages according to the present invention;

FIG. 4 is a side perspective view of an impression coping having features and advantages according to the present invention.

FIG. 5 is a side view of the impression coping of FIG. 4;

FIG. 6 is an opposite side view of the impression coping of FIG. 4;

FIG. 7 is a bottom view of the impression coping of FIG. 4;

FIG. 8 is a top view of the impression coping of FIG. 4;

FIGS. 13A–E are perspective, side, opposite side, bottom, and top views, respectively, of another preferred embodiment of an impression coping having features and advantages according to the present invention;

FIGS. 14A–E are perspective, side, opposite side, bottom, and top views, respectively, of another preferred embodiment of an impression coping having features and advantages according to the present invention;

FIGS. 16A–D are side, opposite side, bottom, and top views, respectively, of another preferred embodiment of an impression coping having features and advantages according to the present invention.

DETAILED DESCRIPTION OF THE PREFERRED EMBODIMENTS

Figure 2A:
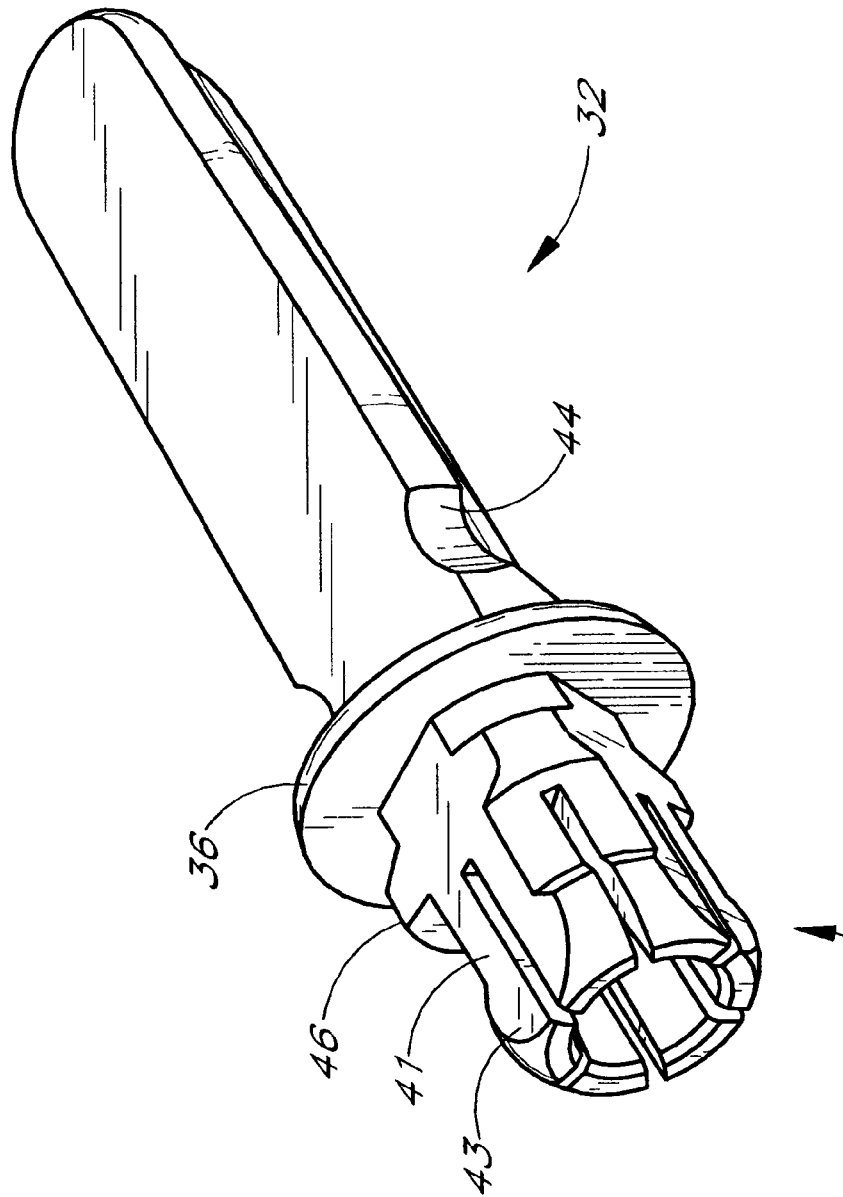
FIG. 2 is a cross-sectional view of the dental implant of FIG. 1 taken along line A—A.
Figure 2B:
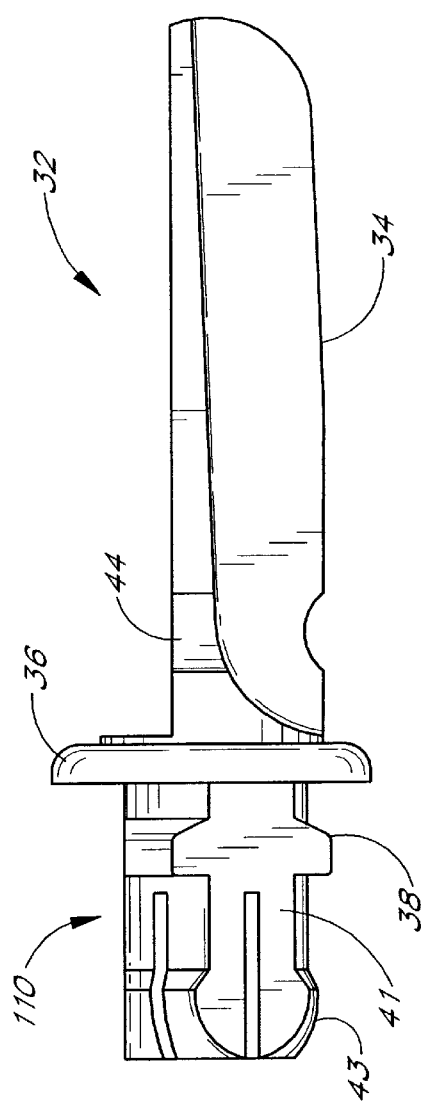
Figure 2C:
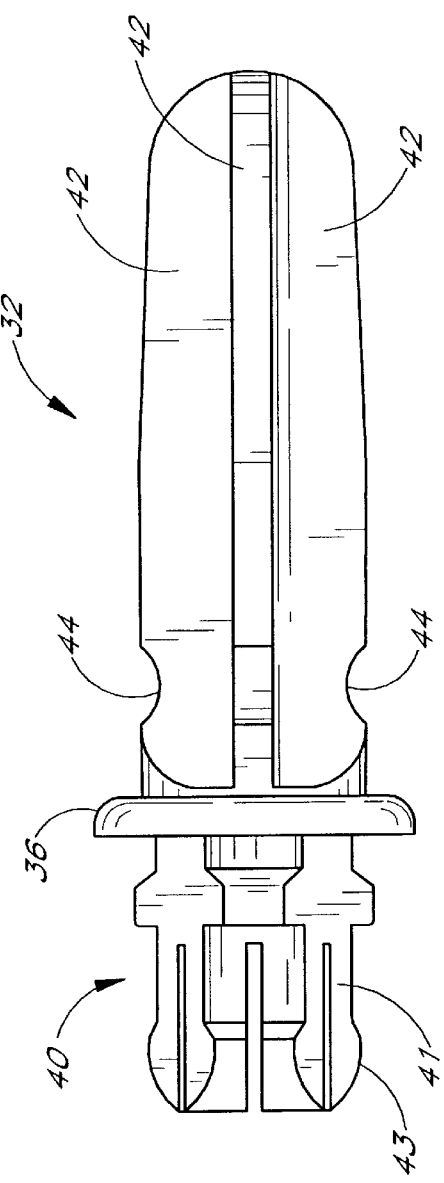
Figure 2D:
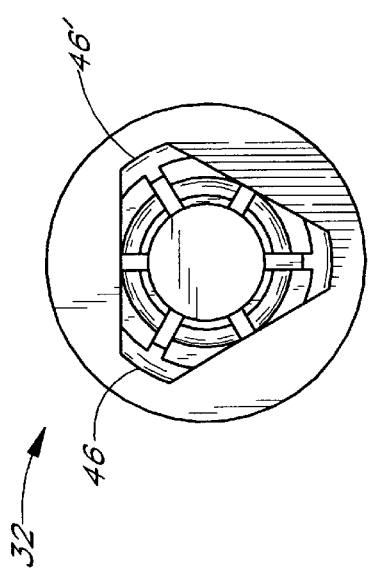
Figure 2E:
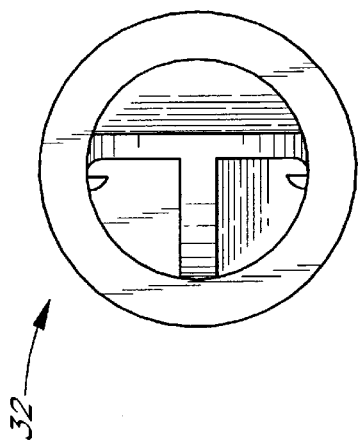
Figure 3A:
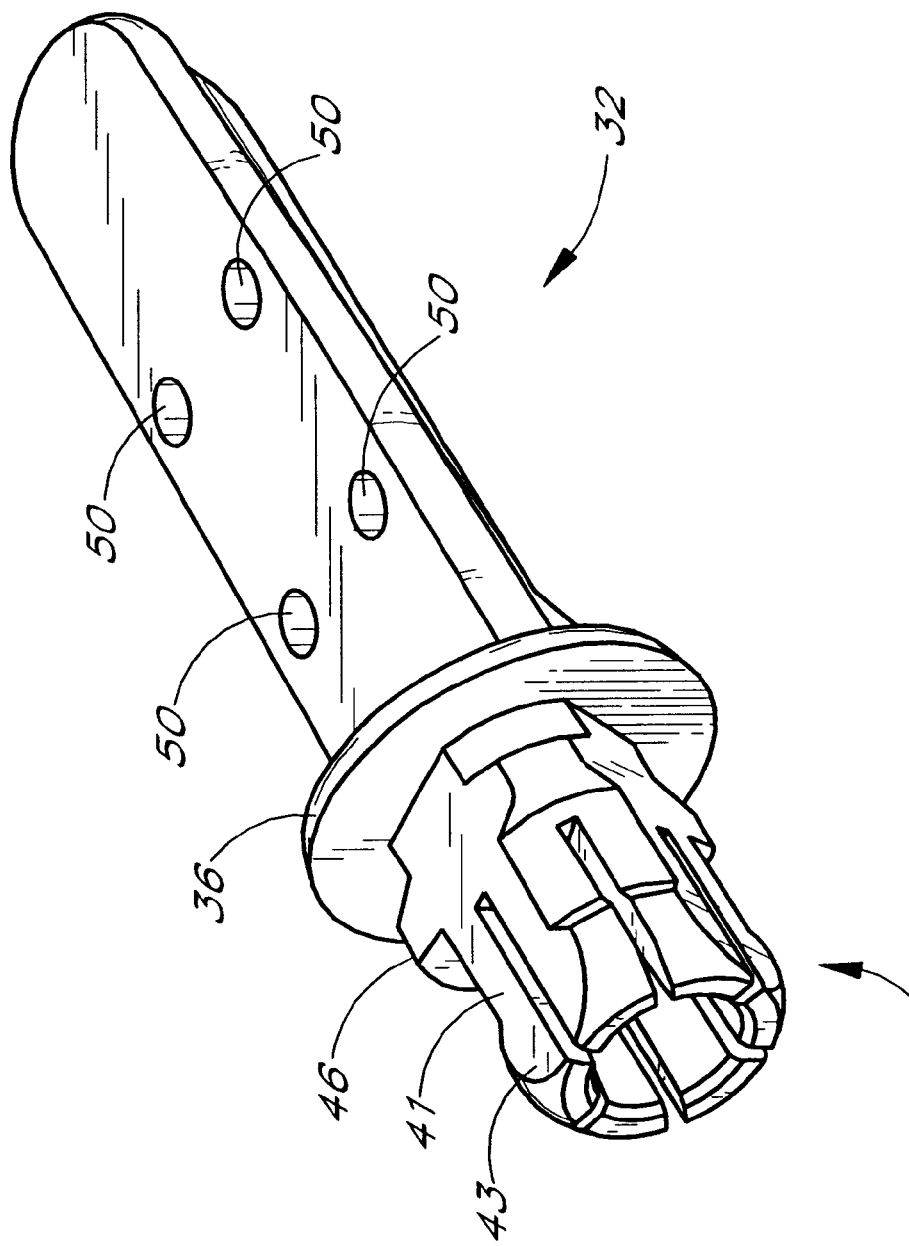
FIG. 3 is a top view of the dental implant of FIG. 1.
Figure 3B:
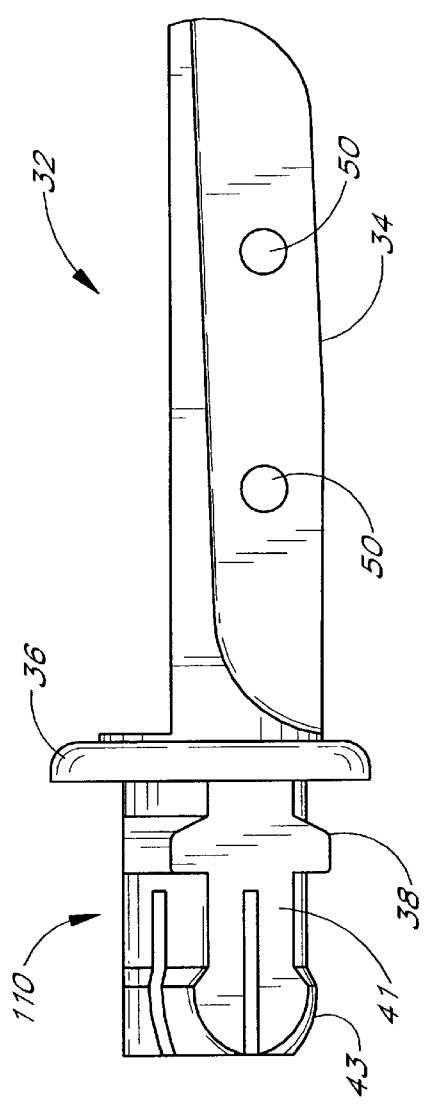
Figure 3C:
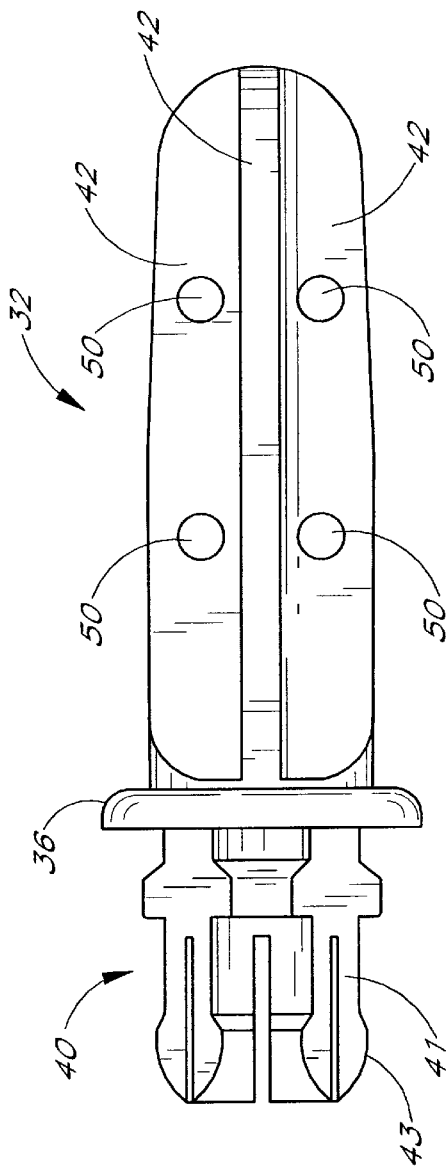
Figure 3D:
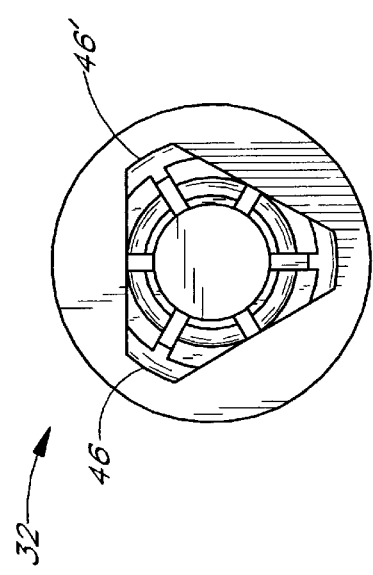
Figure 3E:
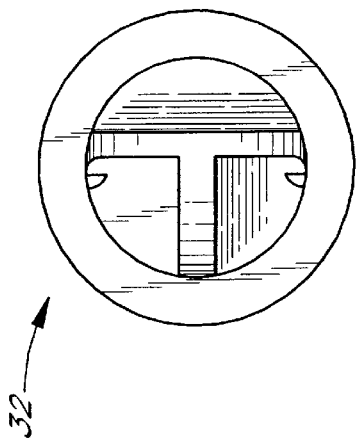

FIGS. 1–3 illustrate a dental implant 10 particularly suited for receiving a snap-in dental impression coping having certain features and advantages according to one embodiment of the present invention. The implant 10 has an outer surface that is preferably divided into three regions: a body portion 12, a neck region 14, and a top portion 16. The body portion 12 preferably includes threads, and represents the portion of the implant 10 that is placed in either the mandible or the maxilla. As shown, the body portion 12 of the implant is substantially cylindrical or slightly tapered; however, the body portion 12 could also assume a conical shape or other known implant shapes, as desired. The threads of the body portion 12 preferably match preformed threads formed along the inner surface of an osteotomy formed in the patient's jawbone. However, the implant 10 could also be designed so as to be self-tapping. Preferably, the top portion 16 of the implant is substantially cylindrical and has a top surface 18 that is substantially flat.

As best seen in FIGS. 2 and 3, the implant 10 includes an inner cavity 20. The inner cavity 20 includes a screw chamber 22, a snapping chamber 24, and an indexing means chamber 26. Preferably, the diameter of the screw chamber 22 is smaller than the diameter of the snapping chamber 24. The snapping chamber 24 preferably includes a recess 25 that has an inner diameter that is slightly larger than the indexing chamber 26.

The screw chamber 22 is preferably sized and configured so as to receive a bolt (not shown). The bolt can be used to temporarily or permanently attach a dental component, such as, for example, a temporary healing abutment or a final restoration to the implant 10. As will be described later, the snapping chamber 24 and the recess 25 are sized and configured to engage a corresponding snapping structure in an impression coping.

The indexing chamber 26 is best seen in FIGS. 2 and 3. In the illustrated arrangement, the indexing chamber 26 is substantially cylindrical with three lobes 28 that extend from the top surface 18 to the bottom of the indexing portion 26. The three lobes 28 are substantially half circular in shape and are symmetrically situated around the perimeter of the indexing portion 26. Preferably, the center of each lobe 28 is 120° apart from each other relative to a center axis 30 of the implant 10. It should be appreciate however, that the indexing chamber 26 can be formed in a wide variety of other suitable symmetric or non-symmetric shapes that may be used with efficacy, giving due consideration to the goals of providing repeatable indexing and anti-rotation of mating components. For example, the indexing chamber 26 could comprise a hexagonal recess or hexagonal protrusion that is situated on the top surface 18 of the implant.

FIGS. 4–8 illustrate one embodiment of an impression coping 32 having features and advantages in accordance with the present invention. Advantageously, due to its snap-in feature the coping 32 may be configured and used as a pick-up type coping that mates with the implant 10 described above, but does not require modification of the impression tray to use. Alternatively, the impression coping 32 may be configured for use as a transfer coping.

As best shown in FIGS. 5 and 6, the impression coping 32 can be divided into four regions: an impression area 34, a cover 36, an indexing area 38, and a snapping portion 40. The illustrated snapping portion 40 consists of a plurality of prongs or tangs 48. Each prong 41 preferably includes a rounded protrusion 43. The protrusions 43 are preferably sized and configured to snap into and resiliently engage the snapping chamber 24 of the implant 10. Accordingly, the protrusions 43 have an outer diameter that is slightly larger than the inner diameter of indexing chamber 26 (see FIGS. 5, 6, 9).

As best shown in FIGS. 4–7, the indexing means 38 has a substantially triangular shape with rounded corners 46. It should be readily apparent that the indexing means 38 of the impression coping 32 is sized and configured to engage the indexing means 26 of a mating implant 10. Like the indexing means of the implant 10, the indexing means 38 may be formed in a wide variety of other shapes that may be used with efficacy, giving due consideration to the goals of providing repeatable indexing and anti-rotation of mating components. For example, the indexing means 38 could comprise a hexagonal boss and/or recess if the implant 10 includes a hexagonal recess and/or boss protrusion, respectively. The cover 36 is substantially circular with a flat surface and preferably has the same outer diameter as the top portion 16 of the implant 10. Accordingly, when the impression coping 32 is snapped into place the flat surface of the cover 36 will be resting in mating flush contact with the implant 10. In this manner, precise orientation and placement of the impression coping 32 is provided.

In the illustrated embodiment, the impression area 34 comprises three flat blade portions or extensions 42 that extend away from the cover 36. The length of the blade is preferably between about 7–15 mm and is most preferably about 11 mm. As viewed from the top (see FIG. 8), the extensions 42 are arranged so as to form an impression pin or blade 34 having a generally "T" shaped cross-section. However, it should be appreciated that the impression coping 32 could include more or less extensions 42, which can be arranged differently. For example, the impression coping 32 could include two extensions that form a "V" shape when viewed from the top. Virtually any conceivable geometry that would facilitate indexing may be utilized. The illustrated geometry is preferred however, because this geometry provides for an impression coping 32 which is easier to manufacture. Additionally, because of the limited amount of material available for the blade or pin 34, a coping 32 which does not have a central bore has more material on the blade or pin to fabricate retentive features such as holes 50, slots 54, criss-crosses or mesh 55 configuration, wings (not shown), button 56 or balls 58 and indexing elements such as annular notches 44. Advantageously, without the center bore the impression coping 32 is smaller and therein more versatile. Thus the coping 32 can be utilized in all areas of the mouth including the lower anterior mandible where interproximal space between abutments is minimal. In addition, the illustrated geometry is preferred because the impression coping 32 is more ergonomic and more efficient for the dentist to place in the mouth. The coping 32 is simply snapped into position instead of the prior art which necessitated placing the coping 32 in the implant 10, holding the coping 32 in place, grasping a screw driver and screw, and screwing the impression coping 32 into the implant 10. However, if it is desired to use the impression coping as a temporary abutment the impression coping may contain a center bore, if desired.

Each blade portion or extension 42 preferably includes a shallow annular recess 44 along preferably the lower portion of the extensions 42. The recess 44 is sized and configured to engage the surrounding impression material, as will be described in more detail below. It should be appreciated that the extensions 42 can include more than one recess 44, if desired. When the impression coping is used in a transfer technique the recesses 44 serve as an insertion index and retention system creating a positive fit and/or tactile feedback when the coping is reinserted into the impression material.

Figure 9A:
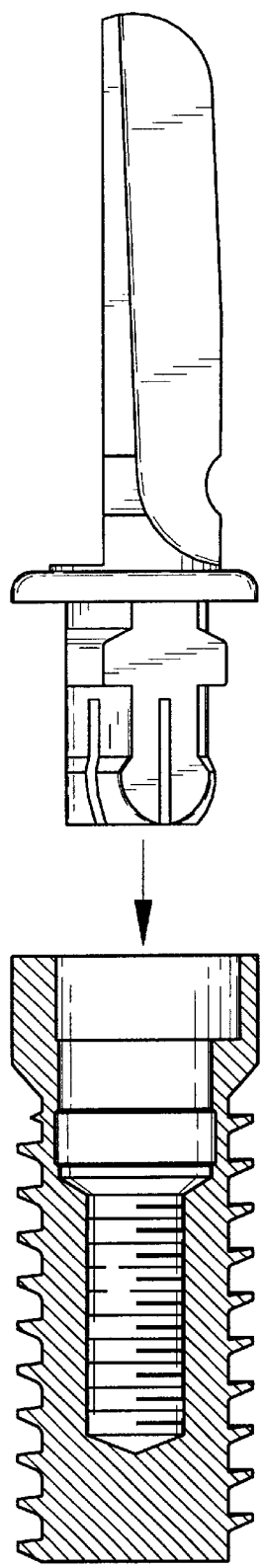
FIGS. 9A–C are partial cross-sectional time assembly views illustrating the impression coping of FIG. 4 being inserted into the implant.
Figure 9B:
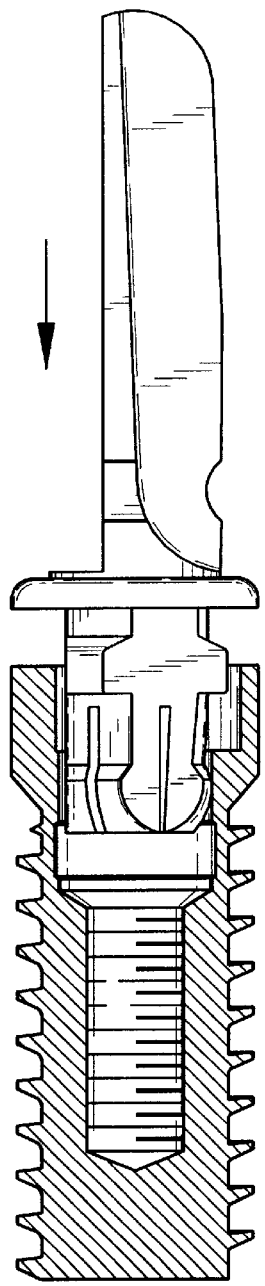
Figure 9C:
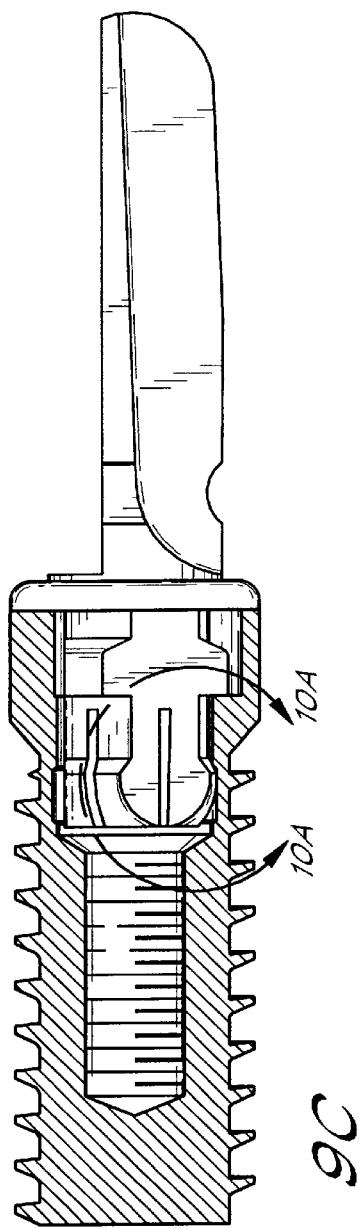
Figure 10A:
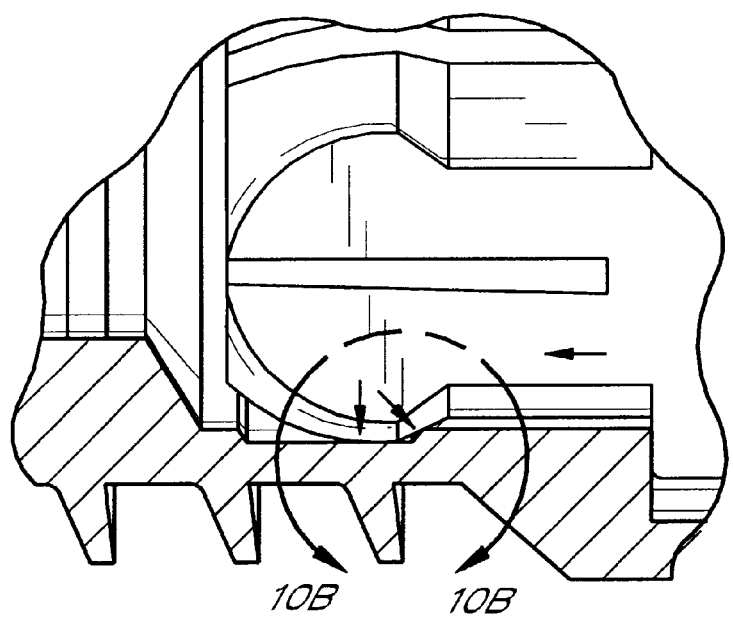
FIGS. 10A and B are detail views of the coping in the snapping chamber of implant assembly.
Figure 10B:
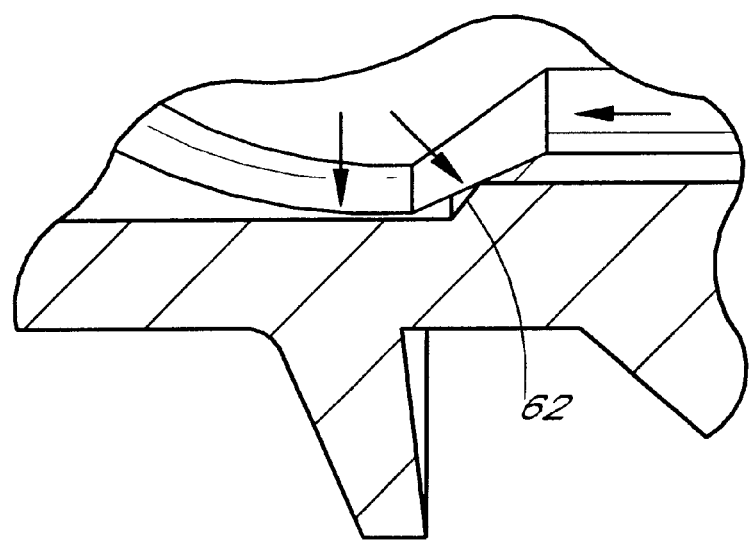

Referring to FIGS. 9A–C, to attach the impression coping 32 to the implant 10 during stage II, the surgeon simply places the impression coping over the implant 10 and pushes the snapping portion 40 of the coping 32 into the implant 10, as will be described in more detail below. As mentioned above, the protrusion 43 of the coping 32 preferably, has at least a slightly larger diameter than the inner diameter of the indexing chamber 26. Accordingly, the snapping portion 40 of the coping 32 is compressed as it passes through the indexing chamber 26 (see FIG. 9A and B). Once the prongs 48 reach the snapping chamber 22, they partially expand forming a snap fit between the coping 32 and the implant 10 (see FIG. 9C). Additionally and advantageously, as the cover is mated against the top surface of the implant, the prongs 48 resiliently engage the slanted inner surface 62 of the snapping chamber 22 (see FIG. 10B). Thus, the pressure exerted against the partially compressed prongs 48 by the slanted inner surface 62 of the snapping chamber 22 creates a reaction downward pulling force. This downward pulling force on the coping 32 causes the mating surface of the cover 36 and the top of the implant 10 to form a seal (see FIG. 9C). Advantageously, this prevents leakage of saliva and bacterial contaminants into the implant and thus prevents infection. This is particularly important if the coping is to be used as a temporary healing abutment.

Clinically and advantageously, the dentist can be assured of the proper placement or seating of the impression coping 32 because as the impression coping 32 is pulled or urged down into the implant 10 the dentist can "feel" the snap fit and hear the audible "click" as the prongs 48 snap into the snapping chamber 22 of the implant. Additionally, the dentist may visually confirm that the impression coping 32 is properly placed or seated by viewing the mated surfaces of the cover 36 and the top of the implant 10 using a dental mirror (see FIG. 9C). If desired, the proper placement or engagement of the coping 32 may be confirmed by attempting to remove the coping 32. A properly seated coping will have perceivable resistance to removal forces as the prongs 48 become compressed as they are pulled back into the indexing chamber 26 (see FIG. 9B).

Figure 11:
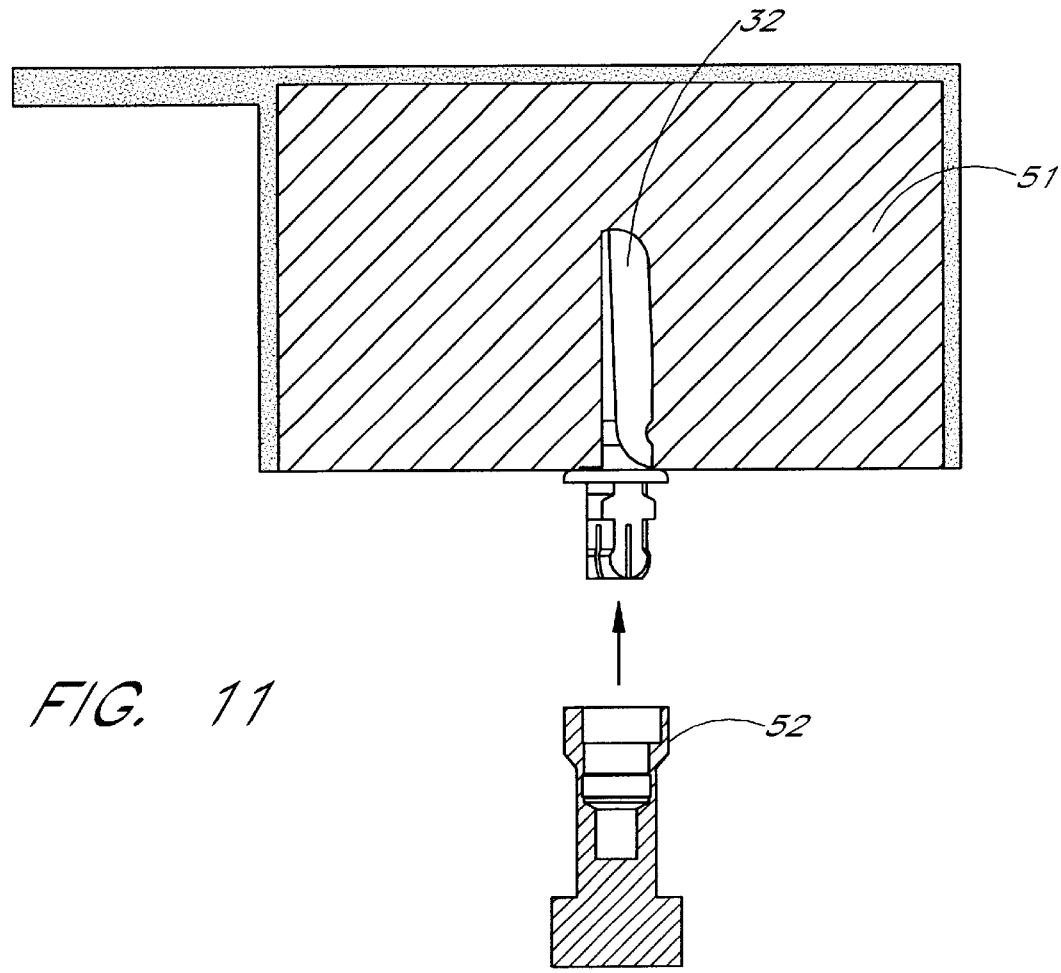
FIG. 11 is a cross-sectional view of an impression tray filled with impression material with an impression coping embedded therein and illustrating the intersection of an implant analog therein.
Figure 13A:
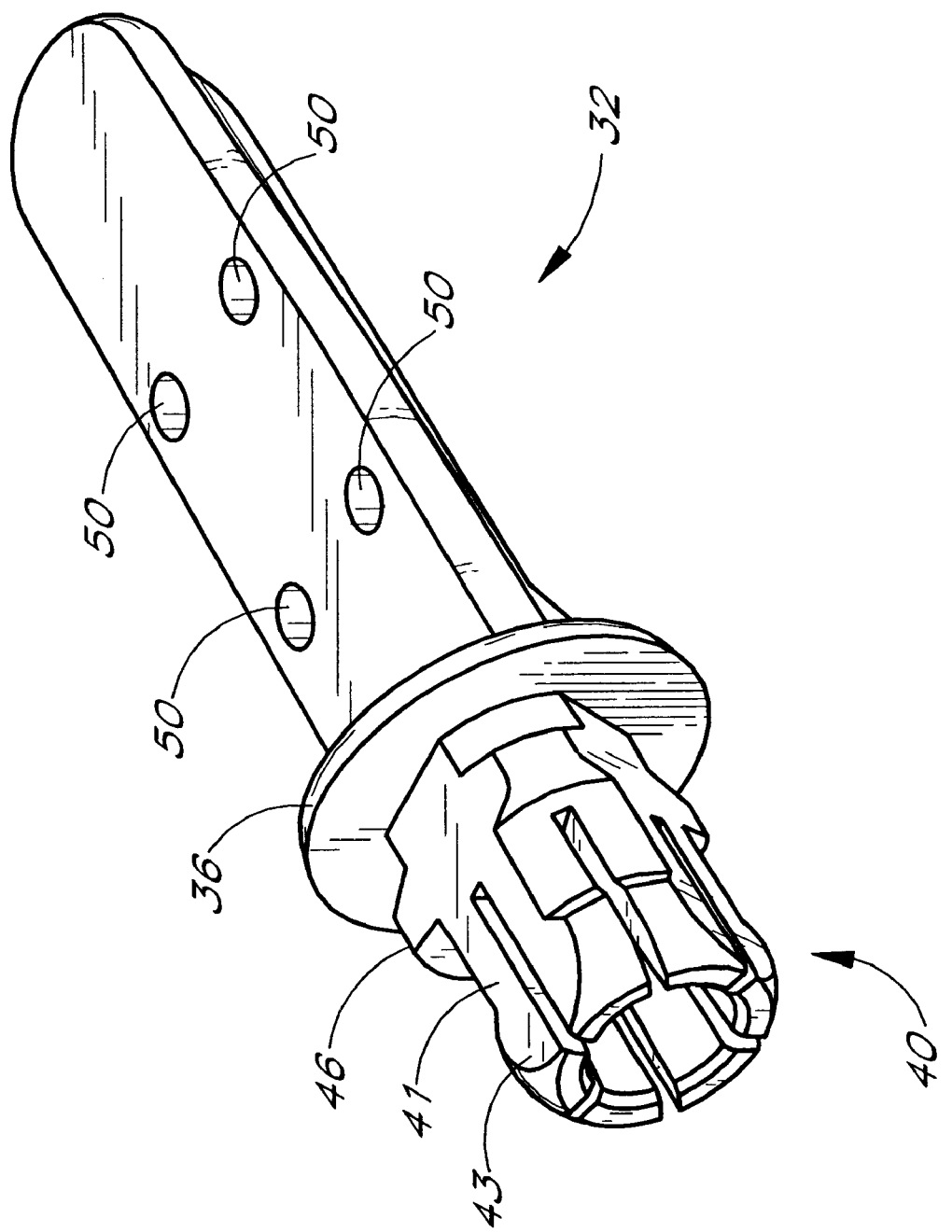
Figure 15A:
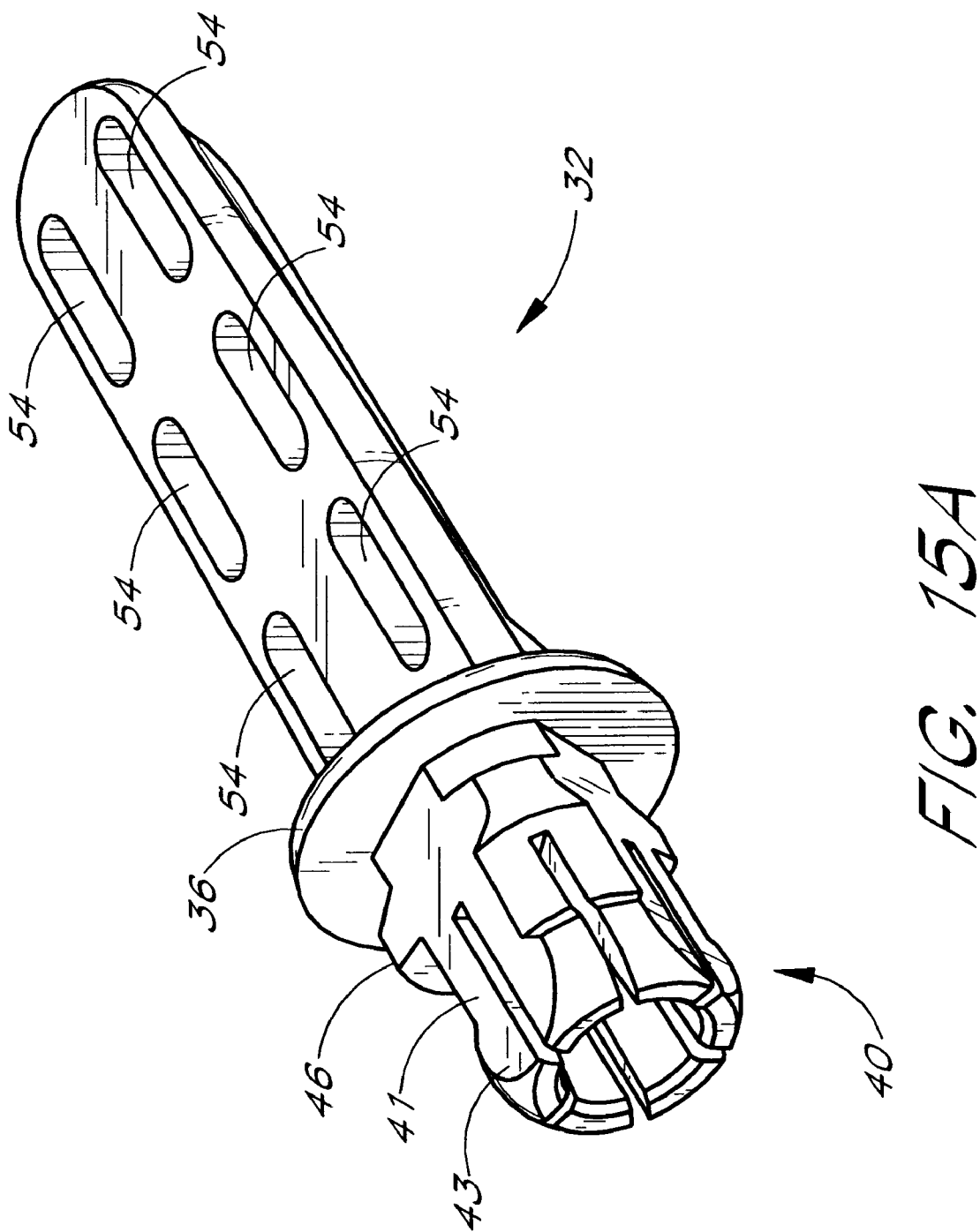
FIGS. 15A–E are perspective, side, opposite side, bottom, and top views, respectively, of another preferred embodiment of an impression coping having features and advantages according to the present invention.
Figure 15B:
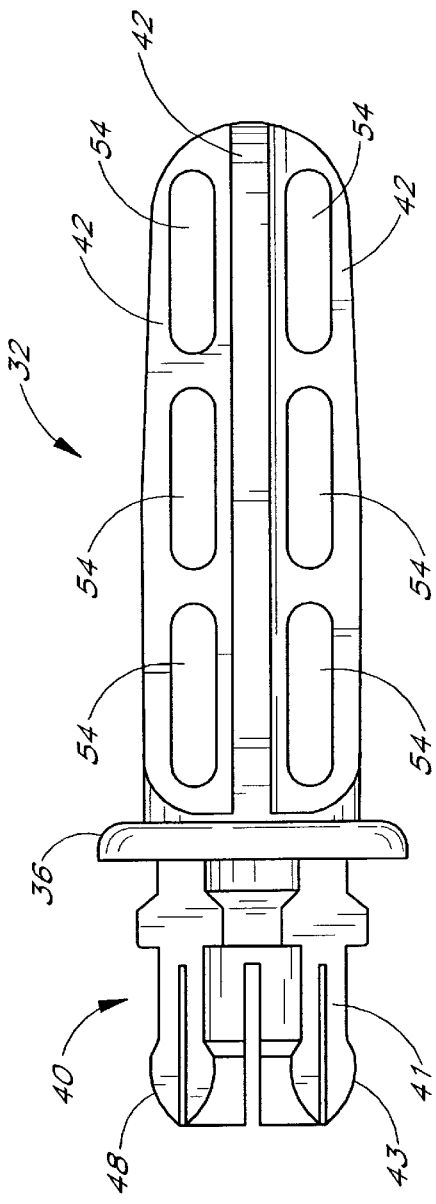
Figure 15C:
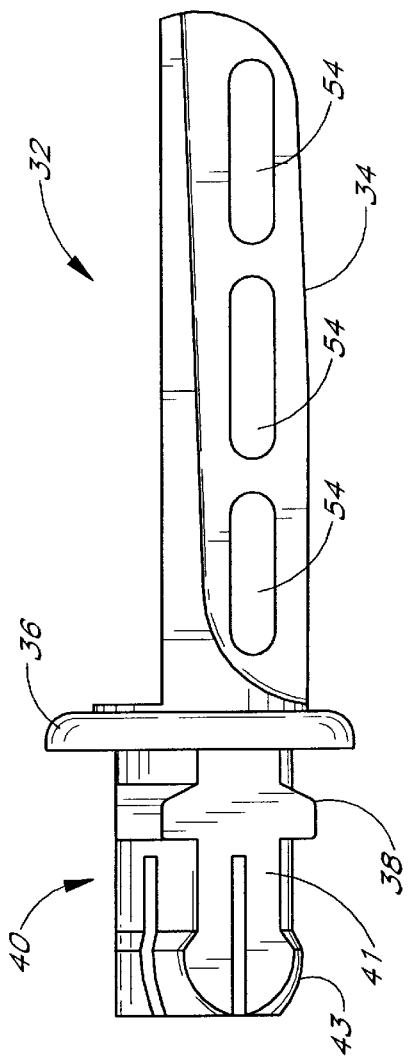
Figure 15E:
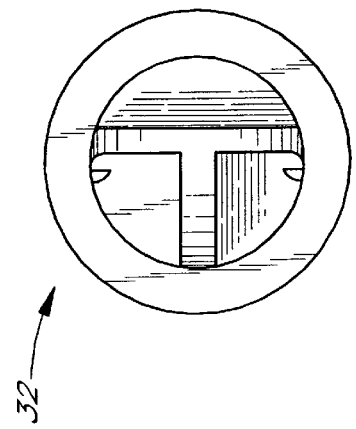
Figure 15D:
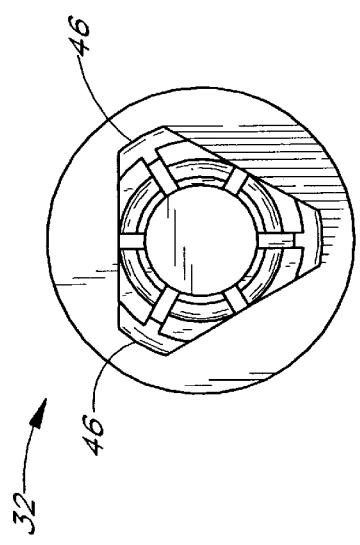

Once the impression coping 32 is attached to the implant 10 a "U" shape impression tray 51 is loaded with an impression material and is placed over the coping, causing the coping to be embedded into the impression material (see FIG. 11). The recesses 44 aid in embedding the impression the coping 32 securely within the impression material and/or function as an insertion indexing system if the coping is removed from the impression material and reinserted. Advantageously, an auxiliary embodiment of the impression coping includes holes 50 (see FIGS. 13A–C), which also aid in embedding the coping 32 securely within the impression material. Another auxiliary embodiment of the impression coping includes slots 54 (see FIGS. 14A–C and 15A–C), which aid in embedding the coping 32 securely within the impression material. Another auxiliary embodiment of the impression coping includes a criss-cross or mesh like structure 55 (see FIGS. 16A–C), which aids in embedding the coping 32 securely within the impression material. After the impression material sets up or hardens, the impression tray is removed from the patient's mouth. In a pick up type impression the coping and implant are configured so that the snapping force created by the snapping portion 40 of the coping 32 and the implant 10 is overcome by the retention force between the impression material and the coping 32. To help ensure that the coping 32 disengages from the implant 10, the protrusions 43 are preferably rounded. Alternatively and/or in addition, the protrusions 43 may comprise a lubricious material such as Teflon or may be coated with or otherwise treated with a diamond-like carbon coating (e.g. amorphous diamond), or a titanium anodic coating.

Figure 12:
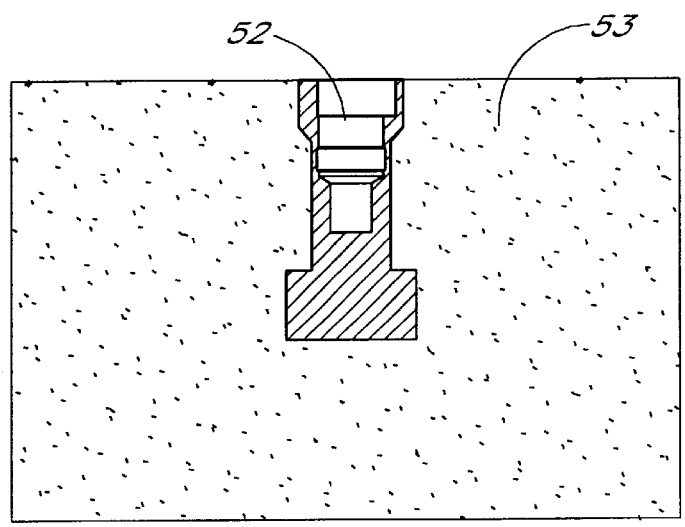
FIG. 12 is a cross-sectional view of an implant analog embedded in dental modeling material forming a positive cast of the implant site.

Advantageously, the coping 32 remains in the impression material and is pulled away from the patient's mouth along with the impression material (see FIG. 11). The impression containing the coping 32 is then delivered to a dental technician for fabrication of the prosthetic tooth. The dental technician attaches an implant analog 52 to the exposed snap portion 40 of the embedded impression coping 32. The model is completed by pouring dental stone or any modeling material in the impression and around the implant analog 52. When the modeling material is set, the model is separated from the impression with the implant analog interlocked in the modeling material 53 (see FIG. 12). The analog 52 is properly positioned in the modeling material 53 to allow the dental technician to accurately create a prosthetic tooth in proper alignment and with proper occlusal length.

FIGS. 13–16 illustrate several alternative preferred embodiments of the impression coping 32. These embodiments are essentially the same as the previously described embodiment, other than for the specific differences noted below. As with the first embodiment described above, in each case the impression coping 32 is designed to snap into a mating implant 10. The main difference is that the impression area 34 does not include annular recess 44 (see FIG. 13). Instead, the impression area 34 includes one or more holes 50 that are designed to engage the impression material. These holes 50 ensure that the impression coping 32 remains embedded in the impression material when the tray is removed from the patient's mouth. Another auxiliary embodiment has slots 54 that are designed to engage the impression material. These slots 54 ensure that the impression coping 32 remains embedded in the impression material when the tray is removed from the patient's mouth (see FIGS. 14 and 15).

Figure 17B:
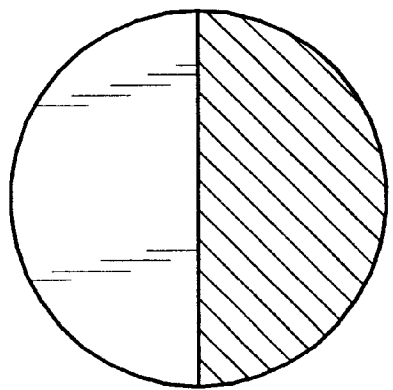
FIGS. 17A and B are perspective, and top views, respectively, of another embodiment of an impression coping having features and advantages according to the present invention.
Figure 17A:
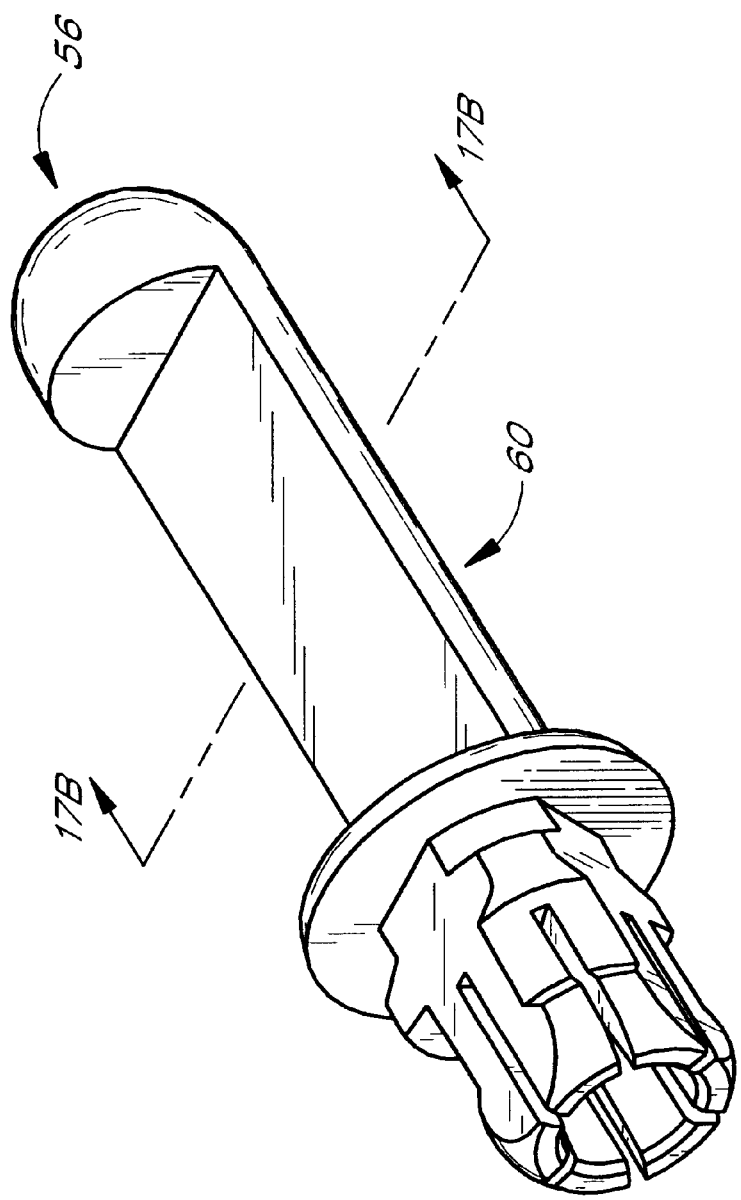
Figure 18B:
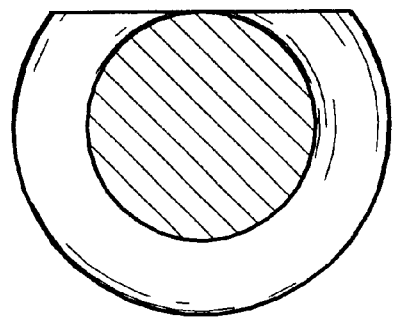
FIGS. 18(A and B) are perspective, and top views, respectively, of another embodiment of an impression coping having features and advantages according to the present invention.
Figure 18A:
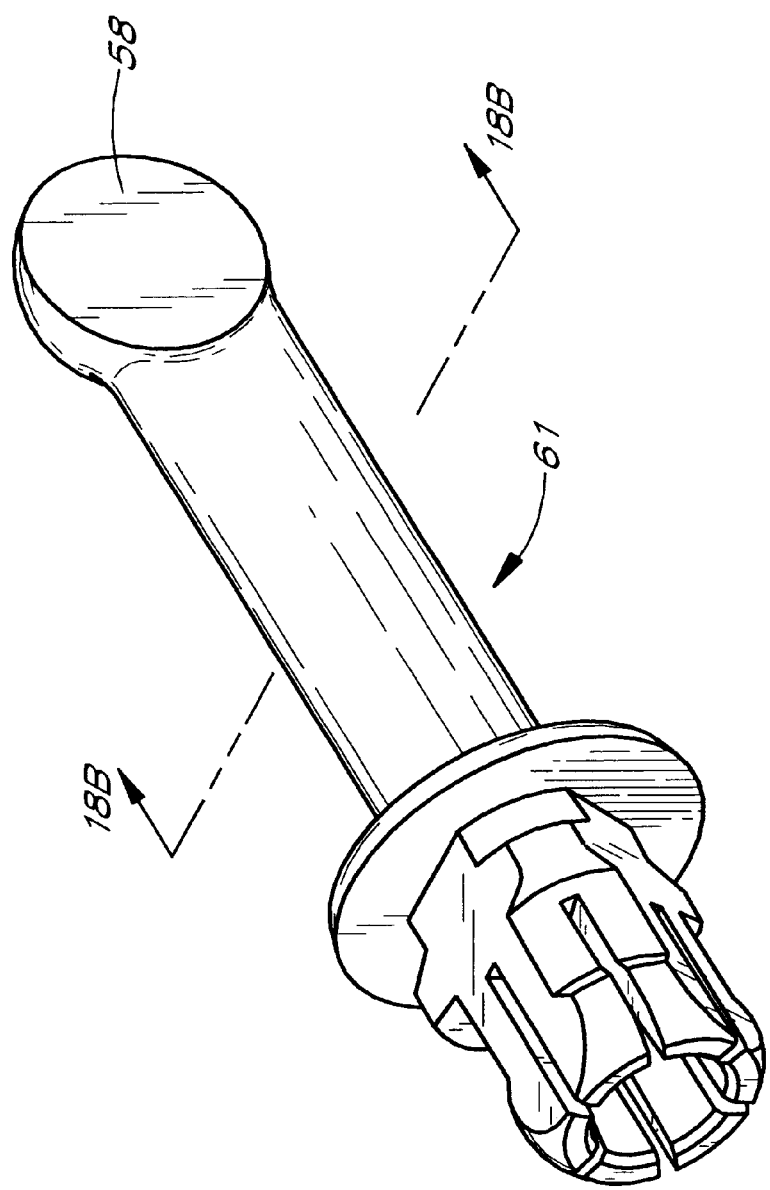

Another auxiliary embodiment has a criss-cross or mesh 55 like configuration that is designed to engage the impression material (see FIG. 16 FIGS. 16A–D). This criss-cross or mesh 55 configuration that is designed to engage the impression material. This criss-cross or mesh 55 configuration ensures that the impression coping 32 remains embedded in the impression material when the tray is removed from the patient's mouth. Another auxiliary embodiment has a D-shaped shaft 60 with an embodiment portion comprising a button or a ball 56 at the distal end to engage the impression material (see FIGS. 17A and B). Another auxiliary embodiment has a round shaft 61 with an embodiment portion comprising a button or ball 58 at the distal end to engage the impression material (see FIGS. 18A and B). The preferred embodiment of the button 56 or ball 58 has a flat side to provide for indexing and anti-rotational properties. Those skilled in the art will appreciate that there are a wide variety of other conceivable geometry's of the impression coping that would facilitate retention by interlocking the impression coping in the impression material that may be utilized.

Preferably for pick-up use, the coping 32 remains in the impression material when the tray is removed from the patient's mouth. Preferably, the withdrawal forces necessary to allow separation of the impression coping 32 and the implant 10 are greater than about 1 lb. to 2 lbs. Accordingly, the unsnapping force between the implant 10 and the coping 32 is desirably less than the retention force between the coping 32 and the impression material. The snapping force is determined primarily by the outer diameter of the protrusions 43, the inner diameters of the recess 25, the inner diameter of the indexing chamber 26, and friction between contacting mated surfaces. To reduce friction, the surface of the protrusions 43 may be coated or otherwise treated with Teflon, diamond-like carbon coating (e.g. amorphous diamond), titanium anodic coating, or any other lubricious coating capable of making the surfaces slide easier. See, for example, U.S. Pat. No. 5,833,463 incorporated herein by reference. To decrease the snapping force, the inner diameter of the protrusions 43 can also be decreased while maintaining the inner diameters of the recess 25 and the indexing chamber 26. The snapping force may also be decreased or controlled by increasing the diameter of the indexing chamber 26 while maintaining the size of the protrusions 43 and the recess 25. Correspondingly, the retention force can be increased by adding additional recesses 25 or holes 50, slots 54, button 56, ball 58, a crisscrossing or mesh configuration 55, or other embedment retention features to the impression area 34, which improves the interlocking of the impression material with the impression coping.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. An impression coping for recording the position and orientation of an implant installed in a patient's jawbone, the impression coping comprising a proximal end and a distal end, said proximal end being configured with one or more resilient prongs adapted to be inserted into a coronal opening formed in said implant and to snappingly engage and secure said coping to said implant, said proximal end further including an indexing boss or recess formed therein for interlockingly engaging a corresponding mating indexing boss or recess formed on said implant, said distal end including an impression portion for embedding in an impression material.

2. The impression coping of claim 1 wherein said coping is configured for use as a transfer coping.

3. The impression coping of claim 2 wherein said impression portion comprises one or more cirumferentially extending ridges for providing a tactile sensory feedback and depth indexing when said impression coping is reinserted into the impression material.

4. The impression coping of claim 1 wherein said coping is configured for use as a pick-up coping.

5. The impression coping of claim 4 wherein said impression portion comprises one or more embedment features for facilitating the gripping and retention of the impression coping within the impression material.

6. The impression coping of claim 5 wherein at least one of said embedment features comprises holes or slots formed in the impression portion of said impression coping for receiving mechanically-interlocking portions of said impression material.

7. The impression coping of claim 5 wherein at least one of said embedment features comprises a protuberant lip for mechanically-interlocking to said impression material and substantially resisting axial extraction forces applied to said impression coping.

8. The impression coping of claim 1 wherein said indexing boss or recess comprises a non-round boss formed on said proximal portion of said impression coping adapted to anti-rotationally mate with a correspondingly-shaped recess formed within said coronal opening of said implant.

9. The impression coping of claim 8 wherein said boss has the general shape of a triangle.

10. The impression coping of claim 8 wherein said boss has the general shape of a hex.

11. The impression coping of claim 1 wherein said impression portion is substantially T-shaped in cross-section.

12. The impression coping of claim 1 wherein said impression portion is substantially D-shaped in cross-section.

13. The impression coping of claim 1 wherein said impression portion is substantially round or tapered in cross-section.

14. The impression coping of claim 1, wherein one or more of said resilient prongs comprises one or more rounded protrusions adapted to snappingly engage one or more corresponding recesses formed within said coronal opening of said implant so as to create a positive indexing and audible/tactile feedback upon inserting said impression coping into the implant.

15. The impression coping of claim 14, wherein said one or more resilient prongs and rounded protrusions are adapted to apply a latent downward force to said impression coping when said impression coping is inserted into said implant.

16. The impression coping of claim 1 in combination with a dental implant adapted to matingly and snappingly receive said impression coping for taking a dental impression.

17. An impression coping for recording the position and orientation of a dental implant installed in a patient's mouth in combination with a dental implant, said implant adapted to matingly and snappingly receive said impression coping, said impression coping comprising a first end adapted to be snappingly and anti-rotationally mated to said implant and comprising a second end including one or more blade portions for embedment in an impression material for taking a dental impression.

18. The impression coping of claim 17 wherein said coping is configured to for use as a pick-up coping.

19. The impression coping of claim 18 wherein said one or more blade portions comprise one or more embedment features for facilitating the gripping and retention of the impression coping within the impression material.

20. The impression coping of claim 19 wherein at least one of said embedment features comprises a protuberant lip for mechanically-interlocking to said impression material and substantially resisting axial extraction forces applied to said impression coping.

21. The impression coping of claim 17 further comprising an indexing boss or recess for anti-rotationally mating with a correspondingly-shaped recess or boss formed within said coronal opening of said implant.

22. The impression coping of claim 21 wherein said boss or recess has the general shape of a triangle.

23. The impression coping of claim 21 wherein said boss or recess has the general shape of a hex.

24. An impression coping for recording the position and orientation of a dental implant installed in a patient's mouth, said impression coping comprising a first end adapted to be snappingly and anti-rotationally mated to said implant and comprising a second end including one or more blade portions for embedment in an impression material for taking a dental impression, wherein said coping is configured for use as a transfer coping.

25. The impression coping of claim 24 wherein said one or more blade portions comprise cirumferentially extending ridges for providing a tactile sensory feedback and depth indexing when said impression coping is reinserted into the impression material.

26. An impression coping for recording the position and orientation of a dental implant installed in a patient's mouth, said impression coping comprising a first end adapted to be snappingly and anti-rotationally mated to said implant and comprising a second end including one or more blade portions for embedment in an impression material for taking a dental impression, wherein said coping is configured to for use as a pick-up coping, said one or more blade portions comprise one or more embedment features for facilitating the gripping and retention of the impression coping within the impression material and at least one of said embedment features comprises holes or slots formed in at least one of said blade portions for receiving mechanically-interlocking portions of said impression material.

27. An impression coping for recording the position and orientation of a dental implant installed in a patient's mouth, said impression coping comprising a first end adapted to be snappingly and anti-rotationally mated to said implant and comprising a second end including one or more blade portions for embedment in an impression material for taking a dental impression, wherein said one or more blade portions intersect to form a substantially T-shaped overall cross-section.

28. An impression coping for recording the position and orientation of a dental implant installed in a patient's mouth, said impression coping comprising a first end adapted to be snappingly and anti-rotationally mated to said implant and comprising a second end including one or more blade portions for embedment in an impression material for taking a dental impression, wherein said proximal end further comprises one or more resilient prongs adapted to snappingly engage one or more corresponding recesses formed within a coronal opening of said implant so as to create a positive indexing and/or audible/tactile feedback upon inserting said impression coping into said implant.

29. The impression coping of claim 28, wherein said one or more resilient prongs are sized and adapted to apply a downward force to said impression coping when said impression coping is inserted into said implant.

30. An impression coping for recording the position and orientation of a dental implant installed in a patient's mouth in combination with a dental implant, said implant adapted to snappingly and anti-rotationally receive said impression coping, said impression coping being snappingly and anti-rotationally mated to said implant and comprising at least one blade portion for embedment in an impression material for taking a dental impression.

31. The impression coping of claim 30 wherein said coping is configured for use as a transfer coping.

32. The impression coping of claim 31 wherein said at least one blade portion comprises a cirumferentially extending ridge for providing a tactile sensory feedback and depth indexing when said impression coping is reinserted into the impression material.

33. The impression coping of claim 32 wherein said coping is configured for use as a pick-up coping.

34. The impression coping of claim 33 wherein said at least one blade portion comprises one or more embedment features for facilitating the gripping and retention of the impression coping within the impression material.

35. The impression coping of claim 34 wherein at least one of said embedment features comprises a protuberant lip for mechanically-interlocking to said impression material and substantially resisting axial extraction forces applied to said impression coping.

36. The impression coping of claim 30 further comprising an indexing boss or recess for anti-rotationally mating with a correspondingly-shaped recess or boss formed within a coronal opening of said implant.

37. The impression coping of claim 36 wherein said boss or recess has the general shape of a triangle.

38. The impression coping of claim 36 wherein said boss or recess has the general shape of a hex.

39. An impression coping for recording the position and orientation of a dental implant installed in a patient's mouth, said impression coping being snappingly and anti-rotationally mated to said implant and comprising at least one blade portion for embedment in an impression material for taking a dental impression, wherein said coping is configured to for use as a pick-up coping, said at least one blade portion comprises one or more embedment features for facilitating the gripping and retention of the impression coping within the impression material and at least one of said embedment features comprises holes or slots formed in said at least one blade portion for receiving mechanically-interlocking portions of said impression material.

40. An impression coping for recording the position and orientation of a dental implant installed in a patient's mouth, said impression coping being snappingly and anti-rotationally mated to said implant and comprising at least one blade portion for embedment in an impression material for taking a dental impression and comprising at least two blade portions intersecting to form a substantially T-shaped cross-section.

41. An impression coping for recording the position and orientation of a dental implant installed in a patient's mouth, said impression coping being snappingly and anti-rotationally mated to said implant and comprising at least one blade portion for embedment in an impression material for taking a dental impression, wherein said proximal end further comprises one or more resilient prongs adapted to snappingly engage one or more corresponding recesses formed within a coronal opening of said implant so as to create a positive indexing and/or audible/tactile feedback upon inserting said impression coping into said implant.

42. The impression coping of claim 41, wherein said one or more resilient prongs are sized and adapted to apply a downward force to said impression coping when said impression coping is inserted into said implant.

43. An impression coping for recording the position and orientation of an implant installed in a patient's jawbone, the impression coping comprising a proximal end and a distal end, said proximal end being sized and adapted to matingly and anti-rotationally engage said implant and having resilient fingers for snappingly mating with corresponding recesses formed within a coronal opening in said implant, said distal end comprising a generally elongated impression portion including one or more substantially flat blade portions extending radially therefrom.

44. The impression coping of claim 43 wherein said coping is configured for use as a transfer coping.

45. The impression coping of claim 44 wherein said one or more blade portions comprise cirumferentially extending ridges for providing a tactile sensory feedback and depth indexing when said impression coping is reinserted into the impression material.

46. The impression coping of claim 44 wherein said coping is configured for use as a pick-up coping.

47. The impression coping of claim 46 wherein said one or more blade portions comprise one or more embedment features for facilitating the gripping and retention of the impression coping within the impression material.

48. The impression coping of claim 47 wherein at least one said embedment features comprises holes or slots formed in at least one of said blade portions for receiving mechanically-interlocking portions of said impression material.

49. The impression coping of claim 47 wherein at least one of said embedment features comprises a protuberant lip for mechanically-interlocking to said impression material and substantially resisting axial extraction forces applied to said impression coping.

50. The impression coping of claim 43 further comprising an indexing boss or recess for anti-rotationally mating with a correspondingly-shaped recess or boss formed within said coronal opening of said implant.

51. The impression coping of claim 50 wherein said boss or recess has the general shape of a triangle.

52. The impression coping of claim 50 wherein said boss or recess has the general shape of a hex.

53. The impression coping of claim 43 wherein said one or more blade portions intersect to form a substantially T-shaped overall cross-section.

54. The impression coping of claim 43, wherein said resilient fingers further comprise one or more rounded protrusions adapted to snappingly engage one or more of said corresponding recesses formed within said coronal opening of said implant so as to create a positive indexing and audible/tactile feedback upon inserting said impression coping into the implant.

55. The impression coping of claim 54, wherein said resilient fingers and protrusions are sized and adapted to apply a downward force to said impression coping when said impression coping is inserted into said implant.

56. The impression coping of claim 43 in combination with a dental implant adapted to matingly and snappingly receive said impression coping for taking a dental impression.

57. An impression coping for taking an impression of an implant installed in a patient's mouth in combination with a dental implant, said dental implant including a coronal opening formed in said dental implant, the impression coping comprising a proximal end and a distal end, said proximal end being sized and adapted to be inserted within said coronal opening and having anti-rotation means cooperating with corresponding anti-rotation means formed on said implant, said means preventing relative rotation of said coping and said implant when said coping is inserted in said implant, said coping further comprising resilient snap means for snappingly engaging corresponding surfaces formed within the coronal opening of said implant, said distal end comprising an impression portion adapted to be embedded in a dental impression material for taking a dental impression thereof.

58. An impression coping for taking an impression of an implant installed in a patient's mouth, said impression coping comprising a proximal end and a distal end, said proximal end being inserted within a coronal opening formed in said implant and having anti-rotation means cooperating with corresponding anti-rotation means formed in said implant, said anti-rotation means cooperating to prevent relative rotation of said coping and said implant, said coping further comprising resilient fingers for engaging corresponding surfaces formed within the coronal opening of said implant, said distal end comprising an impression portion adapted to be embedded in a dental impression material for taking a dental impression thereof.

59. An impression coping for recording the position and orientation of a dental implant installed in a patient's mouth, said impression coping comprising a first end adapted to be snappingly and anti-rotationally mated within a coronal opening of said implant, a top portion adapted to cover said coronal opening, a second end including one or more blade portions that extend from said top portion and are configured for embedment in an impression material for taking a dental impression.

60. The impression coping of claim 59 wherein said coping is configured for use as a transfer coping.

61. The impression coping of claim 60 wherein said one or more blade portions comprise cirumferentially extending ridges for providing a tactile sensory feedback and depth indexing when said impression coping is reinserted into the impression material.

62. The impression coping of claim 59 wherein said coping is configured to for use as a pick-up coping.

63. The impression coping of claim 62 wherein said one or more blade portions comprise one or more embedment features for facilitating the gripping and retention of the impression coping within the impression material.

64. The impression coping of claim 63 wherein at least one of said embedment features comprises holes or slots formed in at least one of said blade portions for receiving mechanically-interlocking portions of said impression material.

65. A method for recording the position and orientation of a dental implant installed in a patient's mouth, comprising:

inserting a proximal end of an impression coping into a coronal opening of said dental implant until said proximal end snappingly engages and secures said impression coping to said dental implant, taking an impression of the patient's mouth by placing an impression tray filed with impression material over the impression coping; and removing the impression tray from the patient's mouth.

66. The method of claim 65, further including configuring said proximal end of said impression coping such that said impression coping disengages from said dental implant when said impression tray is removed from said implant.

67. The method of claim 65, further including configuring said proximal end of said impression coping such that said impression coping remains snappingly engaged with said dental implant when said impression tray is removed from said implant.

68. An impression coping for recording the position and orientation of a dental implant installed in a patient's mouth, said impression coping comprising a first end adapted to be mated to said implant and comprising a second end including one or more blade portions for embedment in an impression material for taking a dental impression, said one or more blade portions comprise one or more embedment features for facilitating the gripping and retention of the impression coping within the impression material and at least one of said embedment features comprises holes or slots formed in at least one of said blade portions for receiving mechanically-interlocking portions of said impression material.

69. An impression coping for recording the position and orientation of a dental implant installed in a patient's mouth, said impression coping comprising a first end adapted to be mated to said implant and comprising a second end including one or more blade portions for embedment in an impression material for taking a dental impression, wherein said one or more blade portions intersect to form a substantially T-shaped overall cross-section.

\* \* \* \* \*

UNITED STATES PATENT AND TRADEMARK OFFICE
CERTIFICATE OF CORRECTION

PATENT NO.     : 6,382,977 B1
DATED          : May 7, 2002
INVENTOR(S)    : Kumar It is certified that error appears in the above-identified patent and that said Letters Patent is hereby corrected as shown below:

<u>Title page,</u>
Item [60], delete "May 2, 2000", insert -- March 2, 2000 --.

Signed and Sealed this

Eleventh Day of March, 2003

JAMES E. ROGAN
*Director of the United States Patent and Trademark Office*